(12) United States Patent
Pereira et al.

(10) Patent No.: US 7,423,018 B2
(45) Date of Patent: Sep. 9, 2008

(54) KINESIN-LIKE PROTEINS AND METHODS OF USE

(75) Inventors: Andrea Pereira, Shrewsbury, MA (US); Diana Bilodeau Wentworth, Northboro, MA (US); Rita Gandhi, Huntington Station, NY (US)

(73) Assignee: University of Massachusetts, Boston, MA (US)

( * ) Notice: Subject to any disclaimer, the term of this patent is extended or adjusted under 35 U.S.C. 154(b) by 452 days.

(21) Appl. No.: 10/735,972

(22) Filed: Dec. 15, 2003

(65) Prior Publication Data

US 2004/0241760 A1     Dec. 2, 2004

Related U.S. Application Data

(60) Provisional application No. 60/433,098, filed on Dec. 13, 2002.

(51) Int. Cl.
*A61K 38/00* (2006.01)
*C12N 9/04* (2006.01)
*C12P 21/06* (2006.01)

(52) U.S. Cl. .................. 514/12; 435/190; 435/69.1

(58) Field of Classification Search ............... 435/190, 435/69.1; 514/12
See application file for complete search history.

(56) References Cited

FOREIGN PATENT DOCUMENTS

| WO | 01/12659 | * | 2/2001 |
| WO | 02/12268 | * | 2/2002 |

OTHER PUBLICATIONS

Rorth, "A modular misexpression screen in *Drosophila* detecting tissue-specific phenotypes," Proc. Natl. Acad. Sci. USA 93:12418-22 (1996).
Sharp et al., "The Bipolar Kinesin, KLP61F, Cross-links Microtubules within Interpolar Microtubule Bundles of *Drosophila* Embryonic Mitotic Spindles," J. Cell. Biol. 144:125-38 (1999).
Sharp et al., "Microtubule Motors in Mitosis," Nature 407:41-47 (2000).
Spradling et al., "Gene disruptions using P transposable elements: an integral component of the *Drosophila* genome project," Proc. Natl. Acad. Sci. USA 92:10824-30 (1995).
Stevenson et al., "Centrosomes and the Scrambled protein coordinate microtubule-independent actin reorganization," Nat. Cell. Biol. 3:68-75 (2001).
*The Development of Drosophila melanogaster*, Cold Spring Harbor Laboratory Press, Plainview, N.Y. vol. I. M. Bate and A.M. Arias, eds., pp. 71-147, 1993.

(Continued)

*Primary Examiner*—Maryam Monshipouri
(74) *Attorney, Agent, or Firm*—Fish & Richardson P.C.

(57) ABSTRACT

The invention relates to methods and compounds for treating subjects who have proliferative disorders. The invention also relates to screening methods for identifying such compounds. The methods and compositions target the activity of the human kinesin-like protein KIF18A (and the KIF18A ortholog, KLP67A) and homologs thereof, and a gene encoding KIF18A or a homologous or orthologous gene. KIF18A and KLP67A are kinesin superfamily (KIF) proteins. Members of the KIF protein family are known to participate in chromosomal and spindle movements during mitosis and meiosis thereby making them attractive targets for treating cancers and the like.

17 Claims, 9 Drawing Sheets

OTHER PUBLICATIONS

Theurauf and Heck "Identification and Characterization of Mitotic Mutations in *Drosophila*," Methods Cell Biol. 61:317-46 (1999).

Tower et al., "Preferential Transposition of *Drosophila* P Elements to Nearby Chromosomal Sites," Genetics 133:347-59 (1993).

Vale and Fletterick, "The design plan of kinesin motors," Annu. Rev. Cell Dev. Biol. 13:745-77 (1997).

Wordeman and Mitchison, "Identification and partial characterization of mitotic centromere-associated kinesin, a kinesin-related protein that associates with centromeres during mitosis," J. Cell. Biol. 128:95-104 (1995).

Zervos et al., "Mxi1, a Protein That Specifically Interacts with Max to Bind Myc-Max Recognition Sites," Cell 72:223-32 (1993).

Better et al., "*Escherichia coli* Secretion of an Active Chimeric Antibody Fragment," Science 240:1041-3 (1988).

Braum et al., "Tumor-Antigen Heterogeneity of Disseminated Breast Cancer Cells: Implications for Immunotherapy of Minimal Residual Disease," Int. J. Cancer 84:1-5 (1999).

Cenci et al., "Chromatin and microtubule organization during premeiotic, meiotic and early postmeiotic stages of *Drosophila melanogaster* spermstogenesis," J. Cell. Sci. 107:3521-34 (1994).

Deák et al., "P-Element Insertion Alleles of Essential Genes on the Third Chromosome of *Drosophila melanogaster*, Correlation of Physical and Cytogenetic Maps in Chromosomal Region 86E-87F," Genetics 147:1697-722 (1997).

Desai et al., "Kim I kinesins are microtubule-destabilizing enzymes," Cell 96:69-78 (1999).

Eggert et al., "Molecular Screening for P-Element Insertions in a Large Genomic Region of *Drosophila melanogaster* Using Polymerase Chain Reaction Mediated by the Vectorette," Genetics 149:1427-34 (1998).

Foe et al., "Microtubules and mitotic cycle phase modulation spatiotemporal distributions of F-actin and myosin II in *Drosophila* syncytial blastoderm embryos," Development 127:1767-87 (2000).

Gandhi et al., "The *Drosophila* kinesin-like protein KLP67A is essential for mitotic and male meiotic spindle assembly," Mol. Biol. Cell 18:121-31 (2004).

Gonzalez et al., "Relationship between chromosome content and nuclear diameter in early spermatids of *Drosophila melanogaster*," Genet. Res. 54:205-12 (1989).

Gunsalus et al., "Mutations in *twinstar*, a *Drosophila* Gene Encoding a Cofilin/ADF Homologue, Result in Defects in Centrosome Migration and Cytokinesis," J. Cell. Biol. 131:1243-59 (1995).

Heck et al., "The Kinesin-like Protein KLP61F is Essential for Mitosis in *Drosophila*," J. Cell. Biol. 123:665-79 (1993).

Heuer et al., "The *Drosophila* homeotic target gene *centrosomin* (*cnn*) encodes a novel centrosomal protein with leucine zippers and maps to a genourio region required for midgut morphogenesis," Development 121:3861-76 (1995).

Hirokawa et al., "Kinesin and dynein superfamily proteins in organelle transport and cell division," Curr. Opin. Cell. Biol. 10:60-73 (1998).

Li and Kaufman, "The Homeotic Target Gene *Centrosomin* Encodes an Essential Centrosomal Component," Cell 85:585-96 (1996).

Mastronarde et al., "Interpolar Spindle Microtubules in FTK cells," J. Cell. Biol. 123:1475-89 (1993).

Miki et al., "All kinesis superfamily protein, KIF, genes in mouse and human," Proc. Natl. Acad. Sci. USA 98:7004-11 (2001).

Nakagawa et al., "Identification and classification of 16 new kinesin superfamily (KIF) proteins in mouse genome," Proc. Natl. Acad. Sci. USA 94:9654-9 (1997).

Nishimura, et al., "Recombinant Human-Mouse Chimeric Monoclonal Antibody Specific for Common Acute Lymphocytic Leukemia Antigen," Cancer Res. 47:999-1005 (1987).

Pereira et al., "Mitochondrial Association of a Plus End-Directed Microtubule Motor Expressed during Mitosis in *Drosophila*," J. Cell. Biol. 136:1081-90 (1997).

\* cited by examiner

Figure 16

SEQ ID NO:1 KIF18A cDNA
GenBank Accession No. AL136819

```
   1 atgtctgtca ctgaggaaga cctgtgccac catatgaaag tagtagttcg tgtacgtccg
  61 gaaacacta aagaaaaagc agctggattt cataaagtgg ttcatgttgt ggataaacat
 121 atcctagttt tgatcccaa acaagaagaa gtcagttttt tccatggaaa gaaaactaca
 181 aatcaaaatg ttataaagaa acaaaataag gatcttaaat ttgtatttga tgctgttttt
 241 gatgaaacgt caactcagtc agaagttttt gaacacacta ctaagccaat tcttcgtagt
 301 tttttgaatg gatataattg cacagtactt gcctatggtg ccactggtgc tgggaagacc
 361 cacactatgc taggatcagc tgatgaacct ggagtgatgt atctaacaat gttacacctt
 421 tacaaatgca tggatgagat taagaagag aaaatatgta gtactgcagt ttcatatctg
 481 gaggtatata atgaacagat tcgtgatctc ttagtaaatt cagggccact tgctgtccgg
 541 gaagataccc aaaaggggt ggtcgttcat ggacttactt tacaccagcc caaatcctca
 601 gaagaaattt tacatttatt ggataatgga aacaaaaaca ggacacaaca tcccactgat
 661 atgaatgcca catcttctcg ttctcatgct gttttccaaa tttacttgcg acaacaagac
 721 aaaacagcaa gtatcaatca aatgtccgt attgccaaga tgtcactcat tgacctggca
 781 ggatctgagc gagcaagtac ttccggtgct aaggggaccc gatttgtaga aggcacaaat
 841 attaatagat cacttttagc tcttgggaat gtcatcaatg ccttagcaga ttcaaagaga
 901 aagaatcagc atatcccta cagaaatagt aagcttactc gcttgttaaa ggattctctt
 961 ggaggaaact gtcaaactat aatgatagct gctgttagtc cttcctctgt attctacgat
1021 gacacatata acactcttaa gtatgctaac cgggcaaagg acattaaatc ttctttgaag
1081 agcaatgttc ttaatgtcaa taatcatata actcaatatg taaagatctg taatgagcag
1141 aaggcagaga ttttattgtt aaaagaaaa ctaaaagcct atgaagaaca gaaagccttc
1201 actaatgaaa atgaccaagc aaagttaatg atttcaaacc ctcaggaaaa agaaatcgaa
1261 aggtttcaag aaatcctgaa ctgcttgttc cagaatcgag aagaaattag acaagaatat
1321 ctgaagttgg aaatgttact taagaaaat gaacttaaat cattctacca caacagtgc
1381 cataaacaaa tagaaatgat gtgttctgaa gacaaagtag aaaaggccac tggaaaacga
1441 gatcatagac ttgcaatgtt gaaaactcgt cgctcctacc tggagaaaag gagggaggag
1501 gaattgaagc aatttgatga aatactaat tggctccatc gtgtcgaaaa agaaatggga
1561 ctcttaagtc aaaacggtca tattccaaag gaactcaaga agatcttca ttgtcaccat
1621 ttgcacctcc agaacaaaga tttgaaagca caaattagac atatgatgga tctagcttgt
1681 cttcaggaac agcaacacag gcagactgaa gcagtattga atgctttact tccaacccta
1741 agaaaacaat attgcacatt aaaagaagcc ggcctgtcaa atgctgcttt tgaatctgac
1801 ttcaaagaga tcgaacattt ggtagagagg aaaaaagtgg tagtttgggc tgaccaaact
1861 gccgaacaac caaagcaaaa cgatctacca gggatttctg ttcttatgac ctttccacaa
1921 cttggaccag ttcagcctat tccttgttgc tcatcttcag gtggaactaa tctggttaag
1981 attcctacag aaaaaagaac tcggagaaaa ctaatgccat ctcccttgaa aggacagcat
2041 actctaaagt ctccaccatc tcaaagtgtg cagctcaatg attctcttag caaagaactt
2101 cagcctattg tatatacacc agaagactgt agaaaagctt ttcaaaatcc gtctacagta
2161 accttaatga accatcatc atttactaca agttttcagg ctatcagctc aaacataaac
2221 agtgataatt gtctgaaaat gttgtgtgaa gtagctatcc ctcataatag aagaaaagaa
2281 tgtggacagg aggacttgga ctctacattt actatatgtg aagcatcaa gagctcgaag
2341 tgtaaattac ccgaacaaga atcactacca aatgataaca aagcattttt acaacggctt
2401 gatccttctt cattctcaac taagcattct atgcctgtac caagcatggt gccatcctac
2461 atggcaatga ctactgctgc caaaaggaaa cggaaattaa caagttctac atcaaacagt
2521 tcgttaactg cagacgtaaa ttctggattt gccaaacgtg ttcgacaaga taattcaagt
2581 gagaagcact acaagaaaaa caaaccaaca atggaacata aagaaacat ctgtaaaata
2641 aatccaagca tggttagaaa atttggaaga aatatttcaa aaggaaatct aagataa
```

Figure 17

SEQ ID NO:2 Amino acid sequence of KIF18A
GenBank Accession No. AL136819

MSVTEEDLCHHMKVVVRVRPENTKEKAAGFHKVVHVVDKHILVFDPKQEEVSF
FHGKKTTNQNVIKKQNKDLKFVFDAVFDETSTQSEVFEHTTKPILRSFLNGYNCT
VLAYGATGAGKTHTMLGSADEPGVMYLTMLHLYKCMDEIKEEKICSTAVSYLE
VYNEQIRDLLVNSGPLAVREDTQKGVVVHGLTLHQPKSSEEILHLLDNGNKNRT
QHPTDMNATSSRSHAVFQIYLRQQDKTASINQNVRIAKMSLIDLAGSERASTSGA
KGTRFVEGTNINRSLLALGNVINALADSKRKNQHIPYRNSKLTRLLKDSLGGNCQ
TIMIAAVSPSSVFYDDTYNTLKYANRAKDIKSSLKSNVLNVNNHITQYVKICNEQ
KAEILLLKEKLKAYEEQKAFTNENDQAKLMISNPQEKEIERFQEILNCLFQNREEI
RQEYLKLEMLLKENELKSFYQQQCHKQIEMMCSEDKVEKATGKRDHRLAMLKT
RRSYLEKRREEELKQFDENTNWLHRVEKEMGLLSQNGHIPKELKKDLHCHHLHL
QNKDLKAQIRHMMDLACLQEQQHRQTEAVLNALLPTLRKQYCTLKEAGLSNAA
FESDFKEIEHLVERKKVVVWADQTAEQPKQNDLPGISVLMTFPQLGPVQPIPCCS
SSGGTNLVKIPTEKRTRRKLMPSPLKGQHTLKSPPSQSVQLNDSLSKELQPIVYTP
EDCRKAFQNPSTVTLMKPSSFTTSFQAISSNINSDNCLKMLCEVAIPHNRRKECGQ
EDLDSTFTICEDIKSSKCKLPEQESLPNDNKDILQRLDPSSFSTKHSMPVPSMVPSY
MAMTTAAKRKRKLTSSTSNSSLTADVNSGFAKRVRQDNSSEKHLQENKPTMEH
KRNICKINPSMVRKFGRNISKGNLR

Figure 18

SEQ ID NO:3 Amino acid sequence of KLP67A
GenBank Accession No. NM_079268

MPSEQHTNIKVAVRVRPYNVRELEQKQRSIIKVMDRSALLFDPDEEDDEFFFQGA
KQPYRDITKRMNKKLTMEFDRVFDIDNSNQDLFEECTAPLVDAVLNGYNCSVFV
YGATGAGKTFTMLGSEAHPGLTYLTMQDLFDKIQAQSDVRKFDVGVSYLEVYN
EHVMNLLTKSGPLKLREDNNGVVVSGLCLTPIYSAEELLRMLMLGNSHRTQHPT
DANAESSRSHAIFQVHIRITERKTDTKRTVKLSMIDLAGSERAASTKGIGVRFKEG
ASINKSLLALGNCINKLADGLKHIPYRDSNLTRILKDSLGGNCRTLMVANVSMSS
LTYEDTYNTLKYASRAKKIRTTLKQNVLKSKMPTEFYVKKIDEVVAENERLKER
NKALEAKATQLERAGNSGFDPLELKTWYSKIDAVYAAARQLQEHVLGMRSKIK
NINYRQTLKKELEEFRKLMCVDQRVCQEDFRRFANYMSTLTSQMEKYKEELPS
WLSKMEIAYQDLESLKREVNKSKAYQILIVYVKYKDLELQLTKQNIFNNHVNAI
NQELVENLDLMRKSFRTACEVLNQTYDRLEDGQKLTPEIEAVFERLLRKMRFAD
SEANTKMAEMNPLAVPVALRSSAQEEEEPTCSLTASAKKRQRQAAQSDDDLHLS
MEDFDSQDTESDSEELHRTFKRPRNLNETQVLGPCSSSSSSSTSSSSSARKALTAT
VTKPRTVQQRLVSDLISDQNVRGGNEKIKKALLKSNHFTAQGLQRTLAAASLAK
ENVKYNANYVRKSPRALMAKALAGTSTLARKPLGSASKEPPLVKFNRAASFRLK
K

Figure 19

SEQ ID NO:4 cDNA of KLP67A
GenBank Accession No. NM_079268

```
   1 atgccttcgg aacagcatac gaatataaaa gtggcggttc gcgtacggcc gtataatgtc
  61 cgtgaattgg agcaaaaaca gcggagtatt atcaaggtca tggatcgttc ggcactgctg
 121 ttcgatcccg acgaggagga cgatgagttc ttctttcagg gcgccaagca accgtaccgc
 181 gacatcacca agcggatgaa caaaaagttg accatggaat tcgacagggt attcgatata
 241 gacaattcca accaggatct gttcgaggag tgcacggcgc cgctggtcga cgcggtgtta
 301 aatggataca actgctcggt atttgtatat ggagccactg gcgccggaaa aacattcaca
 361 atgctgggca gcgaggctca tccgggtctg acctatctta ccatgcaaga tctcttcgat
 421 aagatccaag cgcagagcga cgtgcgcaag ttcgatgtgg gggtatccta tctagaggtg
 481 tacaacgaac atgtgatgaa tctgctaact aaatcgggcc ctttaaaact tcgcgaggac
 541 aacaatggcg tggtggtcag tggtctttgt ctcacgccca tctacagtgc cgaggagctg
 601 ctaagaatgc tgatgctggg caactctcat cgcactcagc accccacaga tgccaatgca
 661 gagagttcca ggtcacatgc catcttccag gtgcacatta ggatcacgga gcgcaagacc
 721 gacaccaaaa gaacggtcaa actatccatg atcgatctgg cgggcagtga gagggcggcc
 781 agtacgaaag gcattggagt gcgattcaag gaaggcgcca gcatcaacaa aagtctctta
 841 gctttgggaa attgcataaa caagctagcc gacggcttaa agcacatccc gtaccgcgac
 901 tcgaacctga cacgcatcct gaaggactcg ttgggcggaa attgtcgcac attgatggtg
 961 gccaatgtct cgatgagctc actgacctat gaagatacct acaacaccct taagtacgct
1021 agccgagcta agaagatacg cacgactctg aaacagaatg tcctcaagtc caagatgcca
1081 accgagttct atgtgaagaa gatcgacgag gtggtagccg agaacgagcg actcaaagag
1141 cgcaacaagg cgctggaggc caaggccact cagttggagc gcgccggcaa tagtggattc
1201 gatccgctgg agcttaagac gtggtacagc aagatagacg ctgtatatgc ggccgcccgg
1261 cagcttcagg agcacgtcct tggtatgcgt agcaagatca agaacatcaa ctaccggcag
1321 acactgaaaa agaactgga ggagttcagg aagctgatgt gtgtcgacca gcgagtgtgc
1381 caggaggact ccgtcgcttt tgcgaactac atgagcacac tgaccagcca gatggagaag
1441 tacaaggagg agttgcccag ctggctgagt aaaatggaga ttgcctacca ggatctagaa
1501 agtctaaagc gagaggttaa caaatcaaag gcctaccaga tactcattgt atacgttaag
1561 tacaaggatc tcgagctgca gctgaccaag cagaatatct ttaacaatca cgtgaacgca
1621 attaaccagg agctggttga gaacttggat ctgatgcgaa agtccttccg aacagcctgc
1681 gaagtgctca accagacgta cgatcgcctc gaggatggtc aaaagctgac gccggaaatt
1741 gaggcggtct tcgaaaggtt gctgcgaaag atgcggttcg ccgattccga ggccaatacc
1801 aaaatggccg agatgaatcc gttggcggtg cctgtggctc tgcgcagcag cgcccaggag
1861 gaagaagagc ccacatgcag cctcacggcc agcgccaaaa agcgacaaag gcaagcggct
1921 cagagcgacg acgatctgca tttgagcatg gaggactttg atagccagga caccgaatca
1981 gattccgagg agctgcacag gacgtttaag aggccacgaa atctaaacga aacgcaggtc
2041 ctgggtccct gcagcagtag ttctagcagc agtacttcta gcagcagtag cgcaaggaag
2101 gcactcacgg cgacggtgac caagccgcga accgtccaac agcgactggt cagcgatctg
2161 atatccgatc agaatgtgcg cggtggcaat gaaaagatca agaaggctct actcaagtcg
2221 aatcacttta cggcgcaagg acttcagaga acgttggcgg ctgcttctct ggccaaggaa
2281 aacgtaaaat acaacgccaa ctatgtgcgc aagagtccac gagcgctaat ggccaaagcc
2341 cttgcaggca cctcgacgct tgcgagaaaa ccgctgggat cggccagtaa ggagccgcct
2401 ttggtcaaat tcaatcgtgc tgcttcgttc cgcctgaaga agtag
```

Figure 20

KLP61F dsRNA (SEQ ID NO:13)

gacgggcaca gggaagaccc acaccatggt gggcaacgag actgccgaac
tgaaatcctc ctgggaagat gactctgaca ttggcatcat accgcgcgct ctgagtcacc
ttttcgatga gctgcgcatg atggaggtgg agtacactat gcgcatttcc tacttggaac
tgtacaatga ggagctgtgc gatctactgt ccaccgatga caccaccaag atacgcattt
tcgatgacag caccaagaag ggatcggtga ttatccaggg cctggaggag ataccagtgc
acagcaagga tgatgtgtac aagctgctgg agaagggaaa ggagcgtcgc aaaacagcca
ctacgctgat gaatgcacag tcctcacgct cccacactgt attttctata gttgtgcaca
tcagggagaa tggcatcgaa ggagaggaca tgctgaaaat cggtaaactg aatctggtgg
atctggcggg cagtgaaaat gtttccaagg ctgggaatga aaaggga

Figure 21

KLP67A dsRNA (SEQ ID NO:14)

gtacggc cgtataatgt ccgtgaattg gagcaaaaac agcggagtat
tatcaaggtc atggatcgtt cggcactgct gttcgatccc gacgaggagg acgatgagtt
cttctttcag ggcgccaagc aaccgtaccg cgacatcacc aagcggatga acaaaaagtt
gaccatggaa ttcgacaggg tattcgatat agacaattcc aaccaggatc tgttcgagga
gtgcacggcg ccgctggtcg acgcggtgtt aaatggatac aactgctcgg tatttgtata
tggagccact ggcgccggaa aaacattcac aatgctgggc agcgaggctc atccgggtct
gacctatctt accatgcaag atctcttcga taagatccaa gcgcagagcg acgtgcgcaa
gttcgatgtg ggggtatcct atctagaggt gtacaacgaa catgtgatga atctgctaac
taaatcgggc cctttaaaac ttcgcgagga caacaatggc gtggtggtca gtgg

SEQUENCE LISTING

```
<160> NUMBER OF SEQ ID NOS: 16

<210> SEQ ID NO 1
<211> LENGTH: 2697
<212> TYPE: DNA
<213> ORGANISM: Homo sapiens
<220> FEATURE:
<221> NAME/KEY: CDS
<222> LOCATION: (1)...(2694)

<400> SEQUENCE: 1 atg tct gtc act gag gaa gac ctg tgc cac cat atg aaa gta gta gtt        48
Met Ser Val Thr Glu Glu Asp Leu Cys His His Met Lys Val Val Val
1               5                   10                  15 cgt gta cgt ccg gaa aac act aaa gaa aaa gca gct gga ttt cat aaa        96
Arg Val Arg Pro Glu Asn Thr Lys Glu Lys Ala Ala Gly Phe His Lys
            20                  25                  30 gtg gtt cat gtt gtg gat aaa cat atc cta gtt ttt gat ccc aaa caa       144
Val Val His Val Val Asp Lys His Ile Leu Val Phe Asp Pro Lys Gln
        35                  40                  45 gaa gaa gtc agt ttt ttc cat gga aag aaa act aca aat caa aat gtt       192
Glu Glu Val Ser Phe Phe His Gly Lys Lys Thr Thr Asn Gln Asn Val
    50                  55                  60 ata aag aaa caa aat aag gat ctt aaa ttt gta ttt gat gct gtt ttt       240
```

|  |  |
|---|---|
| Ile Lys Lys Gln Asn Lys Asp Leu Lys Phe Val Phe Asp Ala Val Phe<br>65                   70                  75                  80 |  |
| gat gaa acg tca act cag tca gaa gtt ttt gaa cac act act aag cca<br>Asp Glu Thr Ser Thr Gln Ser Glu Val Phe Glu His Thr Thr Lys Pro<br>                      85                         90                      95 | 288 |
| att ctt cgt agt ttt ttg aat gga tat aat tgc aca gta ctt gcc tat<br>Ile Leu Arg Ser Phe Leu Asn Gly Tyr Asn Cys Thr Val Leu Ala Tyr<br>                    100                      105                    110 | 336 |
| ggt gcc act ggt gct ggg aag acc cac act atg cta gga tca gct gat<br>Gly Ala Thr Gly Ala Gly Lys Thr His Thr Met Leu Gly Ser Ala Asp<br>            115                      120                      125 | 384 |
| gaa cct gga gtg atg tat cta aca atg tta cac ctt tac aaa tgc atg<br>Glu Pro Gly Val Met Tyr Leu Thr Met Leu His Leu Tyr Lys Cys Met<br>130                    135                        140 | 432 |
| gat gag att aaa gaa gag aaa ata tgt agt act gca gtt tca tat ctg<br>Asp Glu Ile Lys Glu Glu Lys Ile Cys Ser Thr Ala Val Ser Tyr Leu<br>145                    150                      155                  160 | 480 |
| gag gta tat aat gaa cag att cgt gat ctc tta gta aat tca ggg cca<br>Glu Val Tyr Asn Glu Gln Ile Arg Asp Leu Leu Val Asn Ser Gly Pro<br>                      165                      170                    175 | 528 |
| ctt gct gtc cgg gaa gat acc caa aaa ggg gtg gtc gtt cat gga ctt<br>Leu Ala Val Arg Glu Asp Thr Gln Lys Gly Val Val Val His Gly Leu<br>            180                      185                      190 | 576 |
| act tta cac cag ccc aaa tcc tca gaa gaa att tta cat tta ttg gat<br>Thr Leu His Gln Pro Lys Ser Ser Glu Glu Ile Leu His Leu Leu Asp<br>                195                      200                    205 | 624 |
| aat gga aac aaa aac agg aca caa cat ccc act gat atg aat gcc aca<br>Asn Gly Asn Lys Asn Arg Thr Gln His Pro Thr Asp Met Asn Ala Thr<br>210                    215                      220 | 672 |
| tct tct cgt tct cat gct gtt ttc caa att tac ttg cga caa caa gac<br>Ser Ser Arg Ser His Ala Val Phe Gln Ile Tyr Leu Arg Gln Gln Asp<br>225                    230                      235                  240 | 720 |
| aaa aca gca agt atc aat caa aat gtc cgt att gcc aag atg tca ctc<br>Lys Thr Ala Ser Ile Asn Gln Asn Val Arg Ile Ala Lys Met Ser Leu<br>                      245                      250                    255 | 768 |
| att gac ctg gca gga tct gag cga gca agt act tcc ggt gct aag ggg<br>Ile Asp Leu Ala Gly Ser Glu Arg Ala Ser Thr Ser Gly Ala Lys Gly<br>            260                      265                      270 | 816 |
| acc cga ttt gta gaa ggc aca aat att aat aga tca ctt tta gct ctt<br>Thr Arg Phe Val Glu Gly Thr Asn Ile Asn Arg Ser Leu Leu Ala Leu<br>                275                      280                    285 | 864 |
| ggg aat gtc atc aat gcc tta gca gat tca aag aga aag aat cag cat<br>Gly Asn Val Ile Asn Ala Leu Ala Asp Ser Lys Arg Lys Asn Gln His<br>290                    295                      300 | 912 |
| atc cct tac aga aat agt aag ctt act cgc ttg tta aag gat tct ctt<br>Ile Pro Tyr Arg Asn Ser Lys Leu Thr Arg Leu Leu Lys Asp Ser Leu<br>305                    310                      315                  320 | 960 |
| gga gga aac tgt caa act ata atg ata gct gct gtt agt cct tcc tct<br>Gly Gly Asn Cys Gln Thr Ile Met Ile Ala Ala Val Ser Pro Ser Ser<br>                      325                      330                    335 | 1008 |
| gta ttc tac gat gac aca tat aac act ctt aag tat gct aac cgg gca<br>Val Phe Tyr Asp Asp Thr Tyr Asn Thr Leu Lys Tyr Ala Asn Arg Ala<br>            340                      345                    350 | 1056 |
| aag gac att aaa tct tct ttg aag agc aat gtt ctt aat gtc aat aat<br>Lys Asp Ile Lys Ser Ser Leu Lys Ser Asn Val Leu Asn Val Asn Asn<br>                355                      360                    365 | 1104 |
| cat ata act caa tat gta aag atc tgt aat gag cag aag gca gag att<br>His Ile Thr Gln Tyr Val Lys Ile Cys Asn Glu Gln Lys Ala Glu Ile<br>370                    375                      380 | 1152 |

-continued

| | | |
|---|---|---|
| tta ttg tta aaa gaa aaa cta aaa gcc tat gaa gaa cag aaa gcc ttc<br>Leu Leu Leu Lys Glu Lys Leu Lys Ala Tyr Glu Glu Gln Lys Ala Phe<br>385                    390                    395                    400 | 1200 |
| act aat gaa aat gac caa gca aag tta atg att tca aac cct cag gaa<br>Thr Asn Glu Asn Asp Gln Ala Lys Leu Met Ile Ser Asn Pro Gln Glu<br>                 405                    410                    415 | 1248 |
| aaa gaa atc gaa agg ttt caa gaa atc ctg aac tgc ttg ttc cag aat<br>Lys Glu Ile Glu Arg Phe Gln Glu Ile Leu Asn Cys Leu Phe Gln Asn<br>            420                    425                    430 | 1296 |
| cga gaa gaa att aga caa gaa tat ctg aag ttg gaa atg tta ctt aaa<br>Arg Glu Glu Ile Arg Gln Glu Tyr Leu Lys Leu Glu Met Leu Leu Lys<br>            435                    440                    445 | 1344 |
| gaa aat gaa ctt aaa tca ttc tac caa caa cag tgc cat aaa caa ata<br>Glu Asn Glu Leu Lys Ser Phe Tyr Gln Gln Gln Cys His Lys Gln Ile<br>450                    455                    460 | 1392 |
| gaa atg atg tgt tct gaa gac aaa gta gaa aag gcc act gga aaa cga<br>Glu Met Met Cys Ser Glu Asp Lys Val Glu Lys Ala Thr Gly Lys Arg<br>465                    470                    475                    480 | 1440 |
| gat cat aga ctt gca atg ttg aaa act cgt cgc tcc tac ctg gag aaa<br>Asp His Arg Leu Ala Met Leu Lys Thr Arg Arg Ser Tyr Leu Glu Lys<br>                 485                    490                    495 | 1488 |
| agg agg gag gag gaa ttg aag caa ttt gat gag aat act aat tgg ctc<br>Arg Arg Glu Glu Glu Leu Lys Gln Phe Asp Glu Asn Thr Asn Trp Leu<br>            500                    505                    510 | 1536 |
| cat cgt gtc gaa aaa gaa atg gga ctc tta agt caa aac ggt cat att<br>His Arg Val Glu Lys Glu Met Gly Leu Leu Ser Gln Asn Gly His Ile<br>            515                    520                    525 | 1584 |
| cca aag gaa ctc aag aaa gat ctt cat tgt cac cat ttg cac ctc cag<br>Pro Lys Glu Leu Lys Lys Asp Leu His Cys His His Leu His Leu Gln<br>530                    535                    540 | 1632 |
| aac aaa gat ttg aaa gca caa att aga cat atg atg gat cta gct tgt<br>Asn Lys Asp Leu Lys Ala Gln Ile Arg His Met Met Asp Leu Ala Cys<br>545                    550                    555                    560 | 1680 |
| ctt cag gaa cag caa cac agg cag act gaa gca gta ttg aat gct tta<br>Leu Gln Glu Gln Gln His Arg Gln Thr Glu Ala Val Leu Asn Ala Leu<br>                 565                    570                    575 | 1728 |
| ctt cca acc cta aga aaa caa tat tgc aca tta aaa gaa gcc ggc ctg<br>Leu Pro Thr Leu Arg Lys Gln Tyr Cys Thr Leu Lys Glu Ala Gly Leu<br>            580                    585                    590 | 1776 |
| tca aat gct gct ttt gaa tct gac ttc aaa gag atc gaa cat ttg gta<br>Ser Asn Ala Ala Phe Glu Ser Asp Phe Lys Glu Ile Glu His Leu Val<br>            595                    600                    605 | 1824 |
| gag agg aaa aaa gtg gta gtt tgg gct gac caa act gcc gaa caa cca<br>Glu Arg Lys Lys Val Val Val Trp Ala Asp Gln Thr Ala Glu Gln Pro<br>610                    615                    620 | 1872 |
| aag caa aac gat cta cca ggg att tct gtt ctt atg acc ttt cca caa<br>Lys Gln Asn Asp Leu Pro Gly Ile Ser Val Leu Met Thr Phe Pro Gln<br>625                    630                    635                    640 | 1920 |
| ctt gga cca gtt cag cct att cct tgt tgc tca tct tca ggt gga act<br>Leu Gly Pro Val Gln Pro Ile Pro Cys Cys Ser Ser Ser Gly Gly Thr<br>                 645                    650                    655 | 1968 |
| aat ctg gtt aag att cct aca gaa aaa aga act cgg aga aaa cta atg<br>Asn Leu Val Lys Ile Pro Thr Glu Lys Arg Thr Arg Arg Lys Leu Met<br>            660                    665                    670 | 2016 |
| cca tct ccc ttg aaa gga cag cat act cta aag tct cca cca tct caa<br>Pro Ser Pro Leu Lys Gly Gln His Thr Leu Lys Ser Pro Pro Ser Gln<br>            675                    680                    685 | 2064 |
| agt gtg cag ctc aat gat tct ctt agc aaa gaa ctt cag cct att gta<br>Ser Val Gln Leu Asn Asp Ser Leu Ser Lys Glu Leu Gln Pro Ile Val<br>            690                    695                    700 | 2112 |

```
tat aca cca gaa gac tgt aga aaa gct ttt caa aat ccg tct aca gta       2160
Tyr Thr Pro Glu Asp Cys Arg Lys Ala Phe Gln Asn Pro Ser Thr Val
705                 710                 715                 720 acc tta atg aaa cca tca tca ttt act aca agt ttt cag gct atc agc       2208
Thr Leu Met Lys Pro Ser Ser Phe Thr Thr Ser Phe Gln Ala Ile Ser
                725                 730                 735 tca aac ata aac agt gat aat tgt ctg aaa atg ttg tgt gaa gta gct       2256
Ser Asn Ile Asn Ser Asp Asn Cys Leu Lys Met Leu Cys Glu Val Ala
            740                 745                 750 atc cct cat aat aga aga aaa gaa tgt gga cag gag gac ttg gac tct       2304
Ile Pro His Asn Arg Arg Lys Glu Cys Gly Gln Glu Asp Leu Asp Ser
        755                 760                 765 aca ttt act ata tgt gaa gac atc aag agc tcg aag tgt aaa tta ccc       2352
Thr Phe Thr Ile Cys Glu Asp Ile Lys Ser Ser Lys Cys Lys Leu Pro
    770                 775                 780 gaa caa gaa tca cta cca aat gat aac aaa gac att tta caa cgg ctt       2400
Glu Gln Glu Ser Leu Pro Asn Asp Asn Lys Asp Ile Leu Gln Arg Leu
785                 790                 795                 800 gat cct tct tca ttc tca act aag cat tct atg cct gta cca agc atg       2448
Asp Pro Ser Ser Phe Ser Thr Lys His Ser Met Pro Val Pro Ser Met
                805                 810                 815 gtg cca tcc tac atg gca atg act act gct gcc aaa agg aaa cgg aaa       2496
Val Pro Ser Tyr Met Ala Met Thr Thr Ala Ala Lys Arg Lys Arg Lys
            820                 825                 830 tta aca agt tct aca tca aac agt tcg tta act gca gac gta aat tct       2544
Leu Thr Ser Ser Thr Ser Asn Ser Ser Leu Thr Ala Asp Val Asn Ser
        835                 840                 845 gga ttt gcc aaa cgt gtt cga caa gat aat tca agt gag aag cac tta       2592
Gly Phe Ala Lys Arg Val Arg Gln Asp Asn Ser Ser Glu Lys His Leu
    850                 855                 860 caa gaa aac aaa cca aca atg gaa cat aaa aga aac atc tgt aaa ata       2640
Gln Glu Asn Lys Pro Thr Met Glu His Lys Arg Asn Ile Cys Lys Ile
865                 870                 875                 880 aat cca agc atg gtt aga aaa ttt gga aga aat att tca aaa gga aat       2688
Asn Pro Ser Met Val Arg Lys Phe Gly Arg Asn Ile Ser Lys Gly Asn
                885                 890                 895 cta aga taa                                                           2697
Leu Arg <210> SEQ ID NO 2
<211> LENGTH: 898
<212> TYPE: PRT
<213> ORGANISM: Homo sapiens

<400> SEQUENCE: 2

Met Ser Val Thr Glu Glu Asp Leu Cys His His Met Lys Val Val
 1               5                  10                  15

Arg Val Arg Pro Glu Asn Thr Lys Glu Lys Ala Ala Gly Phe His Lys
                20                  25                  30

Val Val His Val Asp Lys His Ile Leu Val Phe Asp Pro Lys Gln
            35                  40                  45

Glu Glu Val Ser Phe Phe Gly Lys Lys Thr Thr Asn Gln Asn Val
        50                  55                  60

Ile Lys Lys Gln Asn Lys Asp Leu Lys Phe Val Phe Asp Ala Val Phe
65                  70                  75                  80

Asp Glu Thr Ser Thr Gln Ser Glu Val Phe Glu His Thr Thr Lys Pro
                85                  90                  95

Ile Leu Arg Ser Phe Leu Asn Gly Tyr Asn Cys Thr Val Leu Ala Tyr
```

-continued

```
                100                 105                 110
Gly Ala Thr Gly Ala Gly Lys Thr His Thr Met Leu Gly Ser Ala Asp
            115                 120                 125
Glu Pro Gly Val Met Tyr Leu Thr Met Leu His Leu Tyr Lys Cys Met
        130                 135                 140
Asp Glu Ile Lys Glu Lys Ile Cys Ser Thr Ala Val Ser Tyr Leu
145                 150                 155                 160
Glu Val Tyr Asn Glu Gln Ile Arg Asp Leu Val Asn Ser Gly Pro
                165                 170                 175
Leu Ala Val Arg Glu Asp Thr Gln Lys Gly Val Val His Gly Leu
            180                 185                 190
Thr Leu His Gln Pro Lys Ser Ser Glu Glu Ile Leu His Leu Leu Asp
        195                 200                 205
Asn Gly Asn Lys Asn Arg Thr Gln His Pro Thr Asp Met Asn Ala Thr
    210                 215                 220
Ser Ser Arg Ser His Ala Val Phe Gln Ile Tyr Leu Arg Gln Gln Asp
225                 230                 235                 240
Lys Thr Ala Ser Ile Asn Gln Asn Val Arg Ile Ala Lys Met Ser Leu
                245                 250                 255
Ile Asp Leu Ala Gly Ser Glu Arg Ala Ser Thr Ser Gly Ala Lys Gly
            260                 265                 270
Thr Arg Phe Val Glu Gly Thr Asn Ile Asn Arg Ser Leu Leu Ala Leu
        275                 280                 285
Gly Asn Val Ile Asn Ala Leu Ala Asp Ser Lys Arg Lys Asn Gln His
    290                 295                 300
Ile Pro Tyr Arg Asn Ser Lys Leu Thr Arg Leu Leu Lys Asp Ser Leu
305                 310                 315                 320
Gly Gly Asn Cys Gln Thr Ile Met Ile Ala Ala Val Ser Pro Ser Ser
                325                 330                 335
Val Phe Tyr Asp Asp Thr Tyr Asn Thr Leu Lys Tyr Ala Asn Arg Ala
            340                 345                 350
Lys Asp Ile Lys Ser Ser Leu Lys Ser Asn Val Leu Asn Val Asn Asn
        355                 360                 365
His Ile Thr Gln Tyr Val Lys Ile Cys Asn Glu Gln Lys Ala Glu Ile
    370                 375                 380
Leu Leu Leu Lys Glu Lys Leu Lys Ala Tyr Glu Glu Gln Lys Ala Phe
385                 390                 395                 400
Thr Asn Glu Asn Asp Gln Ala Lys Leu Met Ile Ser Asn Pro Gln Glu
                405                 410                 415
Lys Glu Ile Glu Arg Phe Gln Glu Ile Leu Asn Cys Leu Phe Gln Asn
            420                 425                 430
Arg Glu Glu Ile Arg Gln Glu Tyr Leu Lys Leu Glu Met Leu Leu Lys
        435                 440                 445
Glu Asn Glu Leu Lys Ser Phe Tyr Gln Gln Gln Cys His Lys Gln Ile
    450                 455                 460
Glu Met Met Cys Ser Glu Asp Lys Val Glu Lys Ala Thr Gly Lys Arg
465                 470                 475                 480
Asp His Arg Leu Ala Met Leu Lys Thr Arg Arg Ser Tyr Leu Glu Lys
                485                 490                 495
Arg Arg Glu Glu Glu Leu Lys Gln Phe Asp Glu Asn Thr Asn Trp Leu
            500                 505                 510
His Arg Val Glu Lys Glu Met Gly Leu Leu Ser Gln Asn Gly His Ile
        515                 520                 525
```

```
Pro Lys Glu Leu Lys Lys Asp Leu His Cys His His Leu His Leu Gln
    530                 535                 540
Asn Lys Asp Leu Lys Ala Gln Ile Arg His Met Met Asp Leu Ala Cys
545                 550                 555                 560
Leu Gln Glu Gln Gln His Arg Gln Thr Glu Ala Val Leu Asn Ala Leu
                565                 570                 575
Leu Pro Thr Leu Arg Lys Gln Tyr Cys Thr Leu Lys Glu Ala Gly Leu
            580                 585                 590
Ser Asn Ala Ala Phe Glu Ser Asp Phe Lys Glu Ile Glu His Leu Val
        595                 600                 605
Glu Arg Lys Lys Val Val Trp Ala Asp Gln Thr Ala Glu Gln Pro
    610                 615                 620
Lys Gln Asn Asp Leu Pro Gly Ile Ser Val Leu Met Thr Phe Pro Gln
625                 630                 635                 640
Leu Gly Pro Val Gln Pro Ile Pro Cys Cys Ser Ser Gly Gly Thr
                645                 650                 655
Asn Leu Val Lys Ile Pro Thr Glu Lys Arg Thr Arg Arg Lys Leu Met
            660                 665                 670
Pro Ser Pro Leu Lys Gly Gln His Thr Leu Lys Ser Pro Pro Ser Gln
        675                 680                 685
Ser Val Gln Leu Asn Asp Ser Leu Ser Lys Glu Leu Gln Pro Ile Val
    690                 695                 700
Tyr Thr Pro Glu Asp Cys Arg Lys Ala Phe Gln Asn Pro Ser Thr Val
705                 710                 715                 720
Thr Leu Met Lys Pro Ser Ser Phe Thr Thr Ser Phe Gln Ala Ile Ser
                725                 730                 735
Ser Asn Ile Asn Ser Asp Asn Cys Leu Lys Met Leu Cys Glu Val Ala
            740                 745                 750
Ile Pro His Asn Arg Arg Lys Glu Cys Gly Gln Glu Asp Leu Asp Ser
        755                 760                 765
Thr Phe Thr Ile Cys Glu Asp Ile Lys Ser Ser Lys Cys Lys Leu Pro
    770                 775                 780
Glu Gln Glu Ser Leu Pro Asn Asp Asn Lys Asp Ile Leu Gln Arg Leu
785                 790                 795                 800
Asp Pro Ser Ser Phe Ser Thr Lys His Ser Met Pro Val Pro Ser Met
                805                 810                 815
Val Pro Ser Tyr Met Ala Met Thr Thr Ala Ala Lys Arg Lys Arg Lys
            820                 825                 830
Leu Thr Ser Ser Thr Ser Asn Ser Ser Leu Thr Ala Asp Val Asn Ser
        835                 840                 845
Gly Phe Ala Lys Arg Val Arg Gln Asp Asn Ser Ser Glu Lys His Leu
    850                 855                 860
Gln Glu Asn Lys Pro Thr Met Glu His Lys Arg Asn Ile Cys Lys Ile
865                 870                 875                 880
Asn Pro Ser Met Val Arg Lys Phe Gly Arg Asn Ile Ser Lys Gly Asn
                885                 890                 895
Leu Arg

<210> SEQ ID NO 3
<211> LENGTH: 814
<212> TYPE: PRT
<213> ORGANISM: Drosophila melanogaster

<400> SEQUENCE: 3
```

```
Met Pro Ser Glu Gln His Thr Asn Ile Lys Val Ala Val Arg Val Arg
 1               5                  10                  15

Pro Tyr Asn Val Arg Glu Leu Glu Gln Lys Gln Arg Ser Ile Ile Lys
             20                  25                  30

Val Met Asp Arg Ser Ala Leu Leu Phe Asp Pro Asp Glu Glu Asp Asp
         35                  40                  45

Glu Phe Phe Gln Gly Ala Lys Gln Pro Tyr Arg Asp Ile Thr Lys
     50                  55                  60

Arg Met Asn Lys Lys Leu Thr Met Glu Phe Asp Arg Val Phe Asp Ile
 65                  70                  75                  80

Asp Asn Ser Asn Gln Asp Leu Phe Glu Glu Cys Thr Ala Pro Leu Val
                 85                  90                  95

Asp Ala Val Leu Asn Gly Tyr Asn Cys Ser Val Phe Val Tyr Gly Ala
             100                 105                 110

Thr Gly Ala Gly Lys Thr Phe Thr Met Leu Gly Ser Glu Ala His Pro
         115                 120                 125

Gly Leu Thr Tyr Leu Thr Met Gln Asp Leu Phe Asp Lys Ile Gln Ala
 130                 135                 140

Gln Ser Asp Val Arg Lys Phe Asp Val Gly Val Ser Tyr Leu Glu Val
145                 150                 155                 160

Tyr Asn Glu His Val Met Asn Leu Leu Thr Lys Ser Gly Pro Leu Lys
                 165                 170                 175

Leu Arg Glu Asp Asn Asn Gly Val Val Ser Gly Leu Cys Leu Thr
                 180                 185                 190

Pro Ile Tyr Ser Ala Glu Glu Leu Leu Arg Met Leu Met Leu Gly Asn
         195                 200                 205

Ser His Arg Thr Gln His Pro Thr Asp Ala Asn Ala Glu Ser Ser Arg
 210                 215                 220

Ser His Ala Ile Phe Gln Val His Ile Arg Ile Thr Glu Arg Lys Thr
225                 230                 235                 240

Asp Thr Lys Arg Thr Val Lys Leu Ser Met Ile Asp Leu Ala Gly Ser
             245                 250                 255

Glu Arg Ala Ala Ser Thr Lys Gly Ile Gly Val Arg Phe Lys Glu Gly
         260                 265                 270

Ala Ser Ile Asn Lys Ser Leu Leu Ala Leu Gly Asn Cys Ile Asn Lys
     275                 280                 285

Leu Ala Asp Gly Leu Lys His Ile Pro Tyr Arg Asp Ser Asn Leu Thr
 290                 295                 300

Arg Ile Leu Lys Asp Ser Leu Gly Gly Asn Cys Arg Thr Leu Met Val
305                 310                 315                 320

Ala Asn Val Ser Met Ser Ser Leu Thr Tyr Glu Asp Thr Tyr Asn Thr
             325                 330                 335

Leu Lys Tyr Ala Ser Arg Ala Lys Lys Ile Arg Thr Thr Leu Lys Gln
         340                 345                 350

Asn Val Leu Lys Ser Lys Met Pro Thr Glu Phe Tyr Val Lys Lys Ile
     355                 360                 365

Asp Glu Val Val Ala Glu Asn Glu Arg Leu Lys Glu Arg Asn Lys Ala
 370                 375                 380

Leu Glu Ala Lys Ala Thr Gln Leu Glu Arg Ala Gly Asn Ser Gly Phe
385                 390                 395                 400

Asp Pro Leu Glu Leu Lys Thr Trp Tyr Ser Lys Ile Asp Ala Val Tyr
             405                 410                 415
```

```
Ala Ala Ala Arg Gln Leu Gln Glu His Val Leu Gly Met Arg Ser Lys
            420                 425                 430

Ile Lys Asn Ile Asn Tyr Arg Gln Thr Leu Lys Lys Glu Leu Glu Glu
435                 440                 445

Phe Arg Lys Leu Met Cys Val Asp Gln Arg Val Cys Gln Glu Asp Phe
    450                 455                 460

Arg Arg Phe Ala Asn Tyr Met Ser Thr Leu Thr Ser Gln Met Glu Lys
465                 470                 475                 480

Tyr Lys Glu Glu Leu Pro Ser Trp Leu Ser Lys Met Glu Ile Ala Tyr
                485                 490                 495

Gln Asp Leu Glu Ser Leu Lys Arg Glu Val Asn Lys Ser Lys Ala Tyr
            500                 505                 510

Gln Ile Leu Ile Val Tyr Val Lys Tyr Lys Asp Leu Glu Leu Gln Leu
        515                 520                 525

Thr Lys Gln Asn Ile Phe Asn Asn His Val Asn Ala Ile Asn Gln Glu
530                 535                 540

Leu Val Glu Asn Leu Asp Leu Met Arg Lys Ser Phe Arg Thr Ala Cys
545                 550                 555                 560

Glu Val Leu Asn Gln Thr Tyr Asp Arg Leu Glu Asp Gly Gln Lys Leu
                565                 570                 575

Thr Pro Glu Ile Glu Ala Val Phe Glu Arg Leu Leu Arg Lys Met Arg
            580                 585                 590

Phe Ala Asp Ser Glu Ala Asn Thr Lys Met Ala Glu Met Asn Pro Leu
        595                 600                 605

Ala Val Pro Val Ala Leu Arg Ser Ser Ala Gln Glu Glu Glu Glu Pro
610                 615                 620

Thr Cys Ser Leu Thr Ala Ser Ala Lys Lys Arg Gln Arg Gln Ala Ala
625                 630                 635                 640

Gln Ser Asp Asp Asp Leu His Leu Ser Met Glu Asp Phe Asp Ser Gln
                645                 650                 655

Asp Thr Glu Ser Asp Ser Glu Glu Leu His Arg Thr Phe Lys Arg Pro
            660                 665                 670

Arg Asn Leu Asn Glu Thr Gln Val Leu Gly Pro Cys Ser Ser Ser Ser
        675                 680                 685

Ser Ser Ser Thr Ser Ser Ser Ser Ala Arg Lys Ala Leu Thr Ala
690                 695                 700

Thr Val Thr Lys Pro Arg Thr Val Gln Gln Arg Leu Val Ser Asp Leu
705                 710                 715                 720

Ile Ser Asp Gln Asn Val Arg Gly Gly Asn Glu Lys Ile Lys Lys Ala
                725                 730                 735

Leu Leu Lys Ser Asn His Phe Thr Ala Gln Gly Leu Gln Arg Thr Leu
            740                 745                 750

Ala Ala Ala Ser Leu Ala Lys Glu Asn Val Lys Tyr Asn Ala Asn Tyr
        755                 760                 765

Val Arg Lys Ser Pro Arg Ala Leu Met Ala Lys Ala Leu Ala Gly Thr
770                 775                 780

Ser Thr Leu Ala Arg Lys Pro Leu Gly Ser Ala Ser Lys Glu Pro Pro
785                 790                 795                 800

Leu Val Lys Phe Asn Arg Ala Ala Ser Phe Arg Leu Lys Lys
                805                 810

<210> SEQ ID NO 4
<211> LENGTH: 2445
<212> TYPE: DNA
```

<213> ORGANISM: Drosophila melanogaster
<220> FEATURE:
<221> NAME/KEY: CDS
<222> LOCATION: (1)...(2442)

<400> SEQUENCE: 4

| | | | | | | | | | | | | | | | | |
|---|---|---|---|---|---|---|---|---|---|---|---|---|---|---|---|---|
| atg | cct | tcg | gaa | cag | cat | acg | aat | ata | aaa | gtg | gcg | gtt | cgc | gta | cgg | 48 |
| Met | Pro | Ser | Glu | Gln | His | Thr | Asn | Ile | Lys | Val | Ala | Val | Arg | Val | Arg | |
| 1 | | | | 5 | | | | | 10 | | | | | 15 | | |
| ccg | tat | aat | gtc | cgt | gaa | ttg | gag | caa | aaa | cag | cgg | agt | att | atc | aag | 96 |
| Pro | Tyr | Asn | Val | Arg | Glu | Leu | Glu | Gln | Lys | Gln | Arg | Ser | Ile | Ile | Lys | |
| | | | 20 | | | | | 25 | | | | | 30 | | | |
| gtc | atg | gat | cgt | tcg | gca | ctg | ctg | ttc | gat | ccc | gac | gag | gag | gac | gat | 144 |
| Val | Met | Asp | Arg | Ser | Ala | Leu | Leu | Phe | Asp | Pro | Asp | Glu | Glu | Asp | Asp | |
| | | 35 | | | | | 40 | | | | | 45 | | | | |
| gag | ttc | ttc | ttt | cag | ggc | gcc | aag | caa | ccg | tac | cgc | gac | atc | acc | aag | 192 |
| Glu | Phe | Phe | Phe | Gln | Gly | Ala | Lys | Gln | Pro | Tyr | Arg | Asp | Ile | Thr | Lys | |
| | 50 | | | | | 55 | | | | | 60 | | | | | |
| cgg | atg | aac | aaa | aag | ttg | acc | atg | gaa | ttc | gac | agg | gta | ttc | gat | ata | 240 |
| Arg | Met | Asn | Lys | Lys | Leu | Thr | Met | Glu | Phe | Asp | Arg | Val | Phe | Asp | Ile | |
| 65 | | | | | 70 | | | | | 75 | | | | | 80 | |
| gac | aat | tcc | aac | cag | gat | ctg | ttc | gag | gag | tgc | acg | gcg | ccg | ctg | gtc | 288 |
| Asp | Asn | Ser | Asn | Gln | Asp | Leu | Phe | Glu | Glu | Cys | Thr | Ala | Pro | Leu | Val | |
| | | | | 85 | | | | | 90 | | | | | 95 | | |
| gac | gcg | gtg | tta | aat | gga | tac | aac | tgc | tcg | gta | ttt | gta | tat | gga | gcc | 336 |
| Asp | Ala | Val | Leu | Asn | Gly | Tyr | Asn | Cys | Ser | Val | Phe | Val | Tyr | Gly | Ala | |
| | | | 100 | | | | | 105 | | | | | 110 | | | |
| act | ggc | gcc | gga | aaa | aca | ttc | aca | atg | ctg | ggc | agc | gag | gct | cat | ccg | 384 |
| Thr | Gly | Ala | Gly | Lys | Thr | Phe | Thr | Met | Leu | Gly | Ser | Glu | Ala | His | Pro | |
| | | 115 | | | | | 120 | | | | | 125 | | | | |
| ggt | ctg | acc | tat | ctt | acc | atg | caa | gat | ctc | ttc | gat | aag | atc | caa | gcg | 432 |
| Gly | Leu | Thr | Tyr | Leu | Thr | Met | Gln | Asp | Leu | Phe | Asp | Lys | Ile | Gln | Ala | |
| | 130 | | | | | 135 | | | | | 140 | | | | | |
| cag | agc | gac | gtg | cgc | aag | ttc | gat | gtg | ggg | gta | tcc | tat | cta | gag | gtg | 480 |
| Gln | Ser | Asp | Val | Arg | Lys | Phe | Asp | Val | Gly | Val | Ser | Tyr | Leu | Glu | Val | |
| 145 | | | | | 150 | | | | | 155 | | | | | 160 | |
| tac | aac | gaa | cat | gtg | atg | aat | ctg | cta | act | aaa | tcg | ggc | cct | tta | aaa | 528 |
| Tyr | Asn | Glu | His | Val | Met | Asn | Leu | Leu | Thr | Lys | Ser | Gly | Pro | Leu | Lys | |
| | | | | 165 | | | | | 170 | | | | | 175 | | |
| ctt | cgc | gag | gac | aac | aat | ggc | gtg | gtg | gtc | agt | ggt | ctt | tgt | ctc | acg | 576 |
| Leu | Arg | Glu | Asp | Asn | Asn | Gly | Val | Val | Val | Ser | Gly | Leu | Cys | Leu | Thr | |
| | | | 180 | | | | | 185 | | | | | 190 | | | |
| ccc | atc | tac | agt | gcc | gag | gag | ctg | cta | aga | atg | ctg | atg | ctg | ggc | aac | 624 |
| Pro | Ile | Tyr | Ser | Ala | Glu | Glu | Leu | Leu | Arg | Met | Leu | Met | Leu | Gly | Asn | |
| | | 195 | | | | | 200 | | | | | 205 | | | | |
| tct | cat | cgc | act | cag | cac | ccc | aca | gat | gcc | aat | gca | gag | agt | tcc | agg | 672 |
| Ser | His | Arg | Thr | Gln | His | Pro | Thr | Asp | Ala | Asn | Ala | Glu | Ser | Ser | Arg | |
| | 210 | | | | | 215 | | | | | 220 | | | | | |
| tca | cat | gcc | atc | ttc | cag | gtg | cac | att | agg | atc | acg | gag | cgc | aag | acc | 720 |
| Ser | His | Ala | Ile | Phe | Gln | Val | His | Ile | Arg | Ile | Thr | Glu | Arg | Lys | Thr | |
| 225 | | | | | 230 | | | | | 235 | | | | | 240 | |
| gac | acc | aaa | aga | acg | gtc | aaa | cta | tcc | atg | atc | gat | ctg | gcg | ggc | agt | 768 |
| Asp | Thr | Lys | Arg | Thr | Val | Lys | Leu | Ser | Met | Ile | Asp | Leu | Ala | Gly | Ser | |
| | | | | 245 | | | | | 250 | | | | | 255 | | |
| gag | agg | gcg | gcc | agt | acg | aaa | ggc | att | gga | gtg | cga | ttc | aag | gaa | ggc | 816 |
| Glu | Arg | Ala | Ala | Ser | Thr | Lys | Gly | Ile | Gly | Val | Arg | Phe | Lys | Glu | Gly | |
| | | | 260 | | | | | 265 | | | | | 270 | | | |
| gcc | agc | atc | aac | aaa | agt | ctc | tta | gct | ttg | gga | aat | tgc | ata | aac | aag | 864 |
| Ala | Ser | Ile | Asn | Lys | Ser | Leu | Leu | Ala | Leu | Gly | Asn | Cys | Ile | Asn | Lys | |
| | | 275 | | | | | 280 | | | | | 285 | | | | |

| | | | | | | | | | | | | | | | | |
|---|---|---|---|---|---|---|---|---|---|---|---|---|---|---|---|---|
| cta | gcc | gac | ggc | tta | aag | cac | atc | ccg | tac | cgc | gac | tcg | aac | ctg | aca | 912 |
| Leu | Ala | Asp | Gly | Leu | Lys | His | Ile | Pro | Tyr | Arg | Asp | Ser | Asn | Leu | Thr | |
| | 290 | | | | 295 | | | | | 300 | | | | | | |
| cgc | atc | ctg | aag | gac | tcg | ttg | ggc | gga | aat | tgt | cgc | aca | ttg | atg | gtg | 960 |
| Arg | Ile | Leu | Lys | Asp | Ser | Leu | Gly | Gly | Asn | Cys | Arg | Thr | Leu | Met | Val | |
| 305 | | | | | 310 | | | | | 315 | | | | | 320 | |
| gcc | aat | gtc | tcg | atg | agc | tca | ctg | acc | tat | gaa | gat | acc | tac | aac | acc | 1008 |
| Ala | Asn | Val | Ser | Met | Ser | Ser | Leu | Thr | Tyr | Glu | Asp | Thr | Tyr | Asn | Thr | |
| | | | | 325 | | | | | 330 | | | | | 335 | | |
| ctt | aag | tac | gct | agc | cga | gct | aag | aag | ata | cgc | acg | act | ctg | aaa | cag | 1056 |
| Leu | Lys | Tyr | Ala | Ser | Arg | Ala | Lys | Lys | Ile | Arg | Thr | Thr | Leu | Lys | Gln | |
| | | | 340 | | | | | 345 | | | | | 350 | | | |
| aat | gtc | ctc | aag | tcc | aag | atg | cca | acc | gag | ttc | tat | gtg | aag | aag | atc | 1104 |
| Asn | Val | Leu | Lys | Ser | Lys | Met | Pro | Thr | Glu | Phe | Tyr | Val | Lys | Lys | Ile | |
| | | 355 | | | | | 360 | | | | | 365 | | | | |
| gac | gag | gtg | gta | gcc | gag | aac | gag | cga | ctc | aaa | gag | cgc | aac | aag | gcg | 1152 |
| Asp | Glu | Val | Val | Ala | Glu | Asn | Glu | Arg | Leu | Lys | Glu | Arg | Asn | Lys | Ala | |
| | 370 | | | | | 375 | | | | | 380 | | | | | |
| ctg | gag | gcc | aag | gcc | act | cag | ttg | gag | cgc | gcc | ggc | aat | agt | gga | ttc | 1200 |
| Leu | Glu | Ala | Lys | Ala | Thr | Gln | Leu | Glu | Arg | Ala | Gly | Asn | Ser | Gly | Phe | |
| 385 | | | | | 390 | | | | | 395 | | | | | 400 | |
| gat | ccg | ctg | gag | ctt | aag | acg | tgg | tac | agc | aag | ata | gac | gct | gta | tat | 1248 |
| Asp | Pro | Leu | Glu | Leu | Lys | Thr | Trp | Tyr | Ser | Lys | Ile | Asp | Ala | Val | Tyr | |
| | | | | 405 | | | | | 410 | | | | | 415 | | |
| gcg | gcc | gcc | cgg | cag | ctt | cag | gag | cac | gtc | ctt | ggt | atg | cgt | agc | aag | 1296 |
| Ala | Ala | Ala | Arg | Gln | Leu | Gln | Glu | His | Val | Leu | Gly | Met | Arg | Ser | Lys | |
| | | | 420 | | | | | 425 | | | | | 430 | | | |
| atc | aag | aac | atc | aac | tac | cgg | cag | aca | ctg | aaa | aaa | gaa | ctg | gag | gag | 1344 |
| Ile | Lys | Asn | Ile | Asn | Tyr | Arg | Gln | Thr | Leu | Lys | Lys | Glu | Leu | Glu | Glu | |
| | | 435 | | | | | 440 | | | | | 445 | | | | |
| ttc | agg | aag | ctg | atg | tgt | gtc | gac | cag | cga | gtg | tgc | cag | gag | gac | ttc | 1392 |
| Phe | Arg | Lys | Leu | Met | Cys | Val | Asp | Gln | Arg | Val | Cys | Gln | Glu | Asp | Phe | |
| | 450 | | | | | 455 | | | | | 460 | | | | | |
| cgt | cgc | ttt | gcg | aac | tac | atg | agc | aca | ctg | acc | agc | cag | atg | gag | aag | 1440 |
| Arg | Arg | Phe | Ala | Asn | Tyr | Met | Ser | Thr | Leu | Thr | Ser | Gln | Met | Glu | Lys | |
| 465 | | | | | 470 | | | | | 475 | | | | | 480 | |
| tac | aag | gag | gag | ttg | ccc | agc | tgg | ctg | agt | aaa | atg | gag | att | gcc | tac | 1488 |
| Tyr | Lys | Glu | Glu | Leu | Pro | Ser | Trp | Leu | Ser | Lys | Met | Glu | Ile | Ala | Tyr | |
| | | | | 485 | | | | | 490 | | | | | 495 | | |
| cag | gat | cta | gaa | agt | cta | aag | cga | gag | gtt | aac | aaa | tca | aag | gcc | tac | 1536 |
| Gln | Asp | Leu | Glu | Ser | Leu | Lys | Arg | Glu | Val | Asn | Lys | Ser | Lys | Ala | Tyr | |
| | | | 500 | | | | | 505 | | | | | 510 | | | |
| cag | ata | ctc | att | gta | tac | gtt | aag | tac | aag | gat | ctc | gag | ctg | cag | ctg | 1584 |
| Gln | Ile | Leu | Ile | Val | Tyr | Val | Lys | Tyr | Lys | Asp | Leu | Glu | Leu | Gln | Leu | |
| | | 515 | | | | | 520 | | | | | 525 | | | | |
| acc | aag | cag | aat | atc | ttt | aac | aat | cac | gtg | aac | gca | att | aac | cag | gag | 1632 |
| Thr | Lys | Gln | Asn | Ile | Phe | Asn | Asn | His | Val | Asn | Ala | Ile | Asn | Gln | Glu | |
| | 530 | | | | | 535 | | | | | 540 | | | | | |
| ctg | gtt | gag | aac | ttg | gat | ctg | atg | cga | aag | tcc | ttc | cga | aca | gcc | tgc | 1680 |
| Leu | Val | Glu | Asn | Leu | Asp | Leu | Met | Arg | Lys | Ser | Phe | Arg | Thr | Ala | Cys | |
| 545 | | | | | 550 | | | | | 555 | | | | | 560 | |
| gaa | gtg | ctc | aac | cag | acg | tac | gat | cgc | ctc | gag | gat | ggt | caa | aag | ctg | 1728 |
| Glu | Val | Leu | Asn | Gln | Thr | Tyr | Asp | Arg | Leu | Glu | Asp | Gly | Gln | Lys | Leu | |
| | | | | 565 | | | | | 570 | | | | | 575 | | |
| acg | ccg | gaa | att | gag | gcg | gtc | ttc | gaa | agg | ttg | ctg | cga | aag | atg | cgg | 1776 |
| Thr | Pro | Glu | Ile | Glu | Ala | Val | Phe | Glu | Arg | Leu | Leu | Arg | Lys | Met | Arg | |
| | | | 580 | | | | | 585 | | | | | 590 | | | |
| ttc | gcc | gat | tcc | gag | gcc | aat | acc | aaa | atg | gcc | gag | atg | aat | ccg | ttg | 1824 |
| Phe | Ala | Asp | Ser | Glu | Ala | Asn | Thr | Lys | Met | Ala | Glu | Met | Asn | Pro | Leu | |
| | | 595 | | | | | 600 | | | | | 605 | | | | |

```
gcg gtg cct gtg gct ctg cgc agc agc gcc cag gag gaa gag ccc      1872
Ala Val Pro Val Ala Leu Arg Ser Ser Ala Gln Glu Glu Glu Pro
610             615                 620 aca tgc agc ctc acg gcc agc gcc aaa aag cga caa agg caa gcg gct  1920
Thr Cys Ser Leu Thr Ala Ser Ala Lys Lys Arg Gln Arg Gln Ala Ala
625                 630                 635                 640 cag agc gac gac gat ctg cat ttg agc atg gag gac ttt gat agc cag  1968
Gln Ser Asp Asp Asp Leu His Leu Ser Met Glu Asp Phe Asp Ser Gln
                645                 650                 655 gac acc gaa tca gat tcc gag gag ctg cac agg acg ttt aag agg cca  2016
Asp Thr Glu Ser Asp Ser Glu Glu Leu His Arg Thr Phe Lys Arg Pro
    660                 665                 670 cga aat cta aac gaa acg cag gtc ctg ggt ccc tgc agc agt agt tct  2064
Arg Asn Leu Asn Glu Thr Gln Val Leu Gly Pro Cys Ser Ser Ser Ser
            675                 680                 685 agc agc agt act tct agc agc agt agc gca agg aag gca ctc acg gcg  2112
Ser Ser Ser Thr Ser Ser Ser Ser Ala Arg Lys Ala Leu Thr Ala
690                 695                 700 acg gtg acc aag ccg cga acc gtc caa cag cga ctg gtc agc gat ctg  2160
Thr Val Thr Lys Pro Arg Thr Val Gln Gln Arg Leu Val Ser Asp Leu
705                 710                 715                 720 ata tcc gat cag aat gtg cgc ggt ggc aat gaa aag atc aag aag gct  2208
Ile Ser Asp Gln Asn Val Arg Gly Gly Asn Glu Lys Ile Lys Lys Ala
                725                 730                 735 cta ctc aag tcg aat cac ttt acg gcg caa gga ctt cag aga acg ttg  2256
Leu Leu Lys Ser Asn His Phe Thr Ala Gln Gly Leu Gln Arg Thr Leu
                740                 745                 750 gcg gct gct tct ctg gcc aag gaa aac gta aaa tac aac gcc aac tat  2304
Ala Ala Ala Ser Leu Ala Lys Glu Asn Val Lys Tyr Asn Ala Asn Tyr
            755                 760                 765 gtg cgc aag agt cca cga gcg cta atg gcc aaa gcc ctt gca ggc acc  2352
Val Arg Lys Ser Pro Arg Ala Leu Met Ala Lys Ala Leu Ala Gly Thr
770                 775                 780 tcg acg ctt gcg aga aaa ccg ctg gga tcg gcc agt aag gag ccg cct  2400
Ser Thr Leu Ala Arg Lys Pro Leu Gly Ser Ala Ser Lys Glu Pro Pro
785                 790                 795                 800 ttg gtc aaa ttc aat cgt gct gct tcg ttc cgc ctg aag aag           2442
Leu Val Lys Phe Asn Arg Ala Ala Ser Phe Arg Leu Lys Lys
                805                 810 tag                                                              2445

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
cacccaaggc tctgctccca caat                                        24

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
cccacatcga atttgcgc                                               18
```

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
agtacggccg tataatgtcc gtg                                          23

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ccactgacca ccacgccatt g                                            21

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gacgggcaca gggaagaccc ac                                           22

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
tcccttttca ttcccagcct tgg                                          23

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
cgaaaaccaa acaagagc                                                18

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
cccacatcga atttgcgc                                                18

<210> SEQ ID NO 13
<211> LENGTH: 517
<212> TYPE: DNA
<213> ORGANISM: Drosophila melanogaster

<400> SEQUENCE: 13

```
gacgggcaca gggaagaccc acaccatggt gggcaacgag actgccgaac tgaaatcctc      60
ctgggaagat gactctgaca ttggcatcat accgcgcgct ctgagtcacc ttttcgatga     120
gctgcgcatg atggaggtgg agtacactat gcgcatttcc tacttggaac tgtacaatga     180
ggagctgtgc gatctactgt ccaccgatga caccaccaag atacgcattt cgatgacag      240 caccaagaag ggatcggtga ttatccaggg cctggaggag ataccagtgc acagcaagga     300
tgatgtgtac aagctgctgg agaagggaaa ggagcgtcgc aaaacagcca ctacgctgat     360
gaatgcacag tcctcacgct cccacactgt attttctata gttgtgcaca tcaggagaa     420 tggcatcgaa ggagaggaca tgctgaaaat cggtaaactg aatctggtgg atctggcggg     480
cagtgaaaat gtttccaagg ctgggaatga aaggga                              517
```

<210> SEQ ID NO 14
<211> LENGTH: 521
<212> TYPE: DNA
<213> ORGANISM: Drosophila melanogaster

<400> SEQUENCE: 14

```
gtacggccgt ataatgtccg tgaattggag caaaaacagc ggagtattat caaggtcatg      60
gatcgttcgg cactgctgtt cgatcccgac gaggaggacg atgagttctt ctttcagggc     120
gccaagcaac cgtaccgcga catcaccaag cggatgaaca aaaagttgac catggaattc     180
gacagggtat tcgatataga caattccaac caggatctgt tcgaggagtg cacggcgccg     240
ctggtcgacg cggtgttaaa tggatacaac tgctcggtat ttgtatatgg agccactggc     300
gccgaaaaaa cattcacaat gctgggcagc gaggctcatc cgggtctgac ctatcttacc     360
atgcaagatc tcttcgataa gatccaagcg cagagcgacg tgcgcaagtt cgatgtgggg     420
gtatcctatc tagaggtgta caacgaacat gtgatgaatc tgctaactaa atcgggccct     480
ttaaaacttc gcgaggacaa caatggcgtg gtggtcagtg g                        521
```

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15

```
ccaccttatg ttatttcatc atg                                              23
```

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16

```
ccttgaatcg cactccaatg c                                                21
```

KINESIN-LIKE PROTEINS AND METHODS OF USE

RELATED APPLICATIONS

This application claims the benefit of U.S. Provisional Application No. 60/433,098, filed Dec. 13, 2002, which is incorporated herein by reference in its entirety.

TECHNICAL FIELD

This invention relates to kinesin-like proteins, and more particularly to the kinesin-like protein KIF18A, and related polypeptides.

BACKGROUND

Kinesin-like proteins (KLPs) play roles in several aspects of spindle assembly and chromosome segregation as well as in some non-mitotic processes (reviewed in Hirokawa et al., *Curr. Opin. Cell Biol.*, 10:60-73, 1998). At the molecular level, all the members of this family share homology with the so-called "motor domain" of the kinesin heavy chain, which is a microtubule activated ATPase. The non-motor domain of these proteins is responsible for cargo attachment; a "cargo" can include any one of a variety of different membranous organelles, signal transduction scaffolding systems, and chromosomes. Kinesins use the energy of ATP hydrolysis to move cargo unidirectionally (toward the plus end) along a microtubule. Thus, kinesins are often called "plus-end" directed motors.

*Drosophila* KLP67A is a plus end-directed motor. Cytological studies have shown that KLP67A is associated with tiny 0.1 micron mitochondria at the plus-ends of the astral spindle fibers (Pereira et al., *J. Cell Biol.*, 136:1081-1090, 1997). A human ortholog of KLP67A is KIF18A (Miki et al., *Proc. Natl. Acad. Sci., USA*, 98:7004-11, 2001).

SUMMARY

The kinesin-like genes KIF18A (in human) and KLP67A (in *Drosophila*) have been found to be involved in processes relating to cell division. Methods and compounds for treating a subject, such as a mammal (e.g., a human), having a proliferative disorder are described herein. The new methods and compounds target the activity of the human kinesin-like gene KIF18A, and homologs and orthologs thereof, including the *Drosophila* ortholog, KLP67A.

New methods are described for identifying compounds that modulate the activity of a KIF18A or KLP67A polypeptide. One exemplary method includes a) obtaining a test cell containing a KIF18A or KLP67A polypeptide and a control cell containing a KIF18A or KLP67A polypeptide; b) incubating the test cell with a test compound; and c) detecting an altered localization of the KIF18A or KLP67A polypeptide in the test cell as compared to the KIF18A or KLP67 polypeptide in the control cell, wherein an altered localization indicates that the test compound modulates activity of the KIF18A or KLP67A polypeptide. For example, the KIF18A polypeptide can have the sequence of GenBank Accession Number AL136819 (SEQ ID NO:2), and the KLP67A polypeptide can have the sequence of GenBank Accession Number NM_079268 (SEQ ID NO:3). In this method, the test compound can be an antisense nucleic acid molecule, a small inhibitory RNA (siRNA), a ribozyme, a triple helix molecule, an antibody, a polypeptide, a peptoid, a polypeptide mimetic, a small inorganic molecule, or a small non-nucleic acid organic molecule.

In certain embodiments, the polypeptide can be localized to a region of a dividing cell other than the distal ends of astral microtubules in the presence of the test compound, and the polypeptide can be localized using immunocytochemistry. In certain embodiments, the polypeptide can be fused to a reporter molecule, such as green fluorescent protein (GFP), β-glucuronidase (GUS), luciferase, chloramphenicol transacetylase (CAT), horseradish peroxidase (HRP), or β-galactosidase.

In another aspect, the invention features methods for identifying a compound that modulates expression of a KIF18A or KLP67A DNA sequence, by a) providing a test cell comprising a nucleic acid that expresses the KIF18A or KLP67A polypeptide and a control cell containing a nucleic acid that expresses the KIF18A or KLP67A polypeptide; b) incubating the test cell with a test compound; and c) detecting an increase or decrease in a KIF18A or KLP67A RNA or polypeptide population as compared to a KIF18A or KLP67A RNA or polypeptide population in a control cell; wherein an increase or decrease in the KIF18A or KLP67A RNA population indicates that expression of the KIF18A or KLP67A DNA is modulated by the test compound. In these methods, the increase or decrease in the RNA population can be assayed by Northern blot, RT-PCR, or microarray analysis, and the increase or decrease in the KIF18A or KLP67A polypeptide population can be assayed by Western blot or ELISA.

The invention also provides various methods of assaying for modulation of activity (or expression) of a KIF18A polypeptide in a test cell. Some of these methods include (a) providing a dividing test cell containing a KIF18A polypeptide (or nucleic acid) and a dividing control cell containing a KIF18A polypeptide (or nucleic acid); (b) measuring spindle length in the dividing test cell and the dividing control cell; and (c) determining either (i) the amount of KIF18A polypeptide in the test cell and the control cell, or (ii) the location of KIF18A polypeptide in the test cell and the control cell, or both (i) and (ii); wherein the occurrence of a longer or shorter spindle in the test cell as compared to the control cell, and either (i) the amount of KIF18A polypeptide is different than the amount of KIF18A polypeptide in the control cell, or (ii) the location of KIF18A polypeptide in the test cell is different than the location of KIF18A polypeptide in the control cell, or both (i) and (ii), is an indication that the activity of the KIF18A polypeptide in the test cell is different than the activity of a KIF18A polypeptide in the control cell. For example, the spindle length of the test cell can be increased or decreased by 45-100%, as compared to the spindle length of the control cell.

In these methods, one can further determine whether a KIF18A polypeptide from the test cell contains an altered amino acid compared to a wild type KIF18A polypeptide.

In another version of the methods for assaying for modulation of activity of a KIF18A polypeptide, the methods include (a) providing a dividing test cell containing a KIF18A polypeptide and a dividing control cell containing a KIF18A polypeptide; (b) measuring the angle between two ectopically localized prophase centrosomes in the dividing test cell; and (c) determining either (i) the amount of KIF18A polypeptide in the test cell and the control cell, or (ii) the location of KIF18A polypeptide in the test cell and in the control cell, or both (i) and (ii); wherein the occurrence of a 1-155° angle between the two prophase centrosomes in the dividing cell, and either (i) the amount of KIF18A polypeptide is different than the amount of KIF18A polypeptide in the control cell, or (ii) the location of KIF18A polypeptide in the test cell is different than the location of KIF18A polypeptide in the control cell, or both (i) and (ii), indicates that the activity of the KIF18A polypeptide in the test cell is different than the activity of a KIF18A polypeptide in the control cell.

In these methods, the angle between the two prophase centrosomes in the dividing test cell can range from 130-154°, and the centrosomes can be localized by using an anti-centrosomin antibody and immunocytochemistry.

Another method includes a) providing a dividing test cell containing a KIF18A polypeptide and a dividing control cell containing a KIF18A polypeptide; (b) determining the shape of a spindle or astral microtubule in the dividing test cell and the dividing control cell; and (c) determining either (i) the amount of KIF18A polypeptide in the test cell and the control cell, or (ii) the location of KIF18A polypeptide in the test cell and the control cell, or both (i) and (ii); wherein the occurrence of a spindle or astral microtubule in the dividing test cell that is shaped differently than a spindle or astral microtubule in the control test cell, and either (i) the amount of KIF18A polypeptide is different than the amount of KIF18A polypeptide in the control cell, or (ii) the location of KIF18A polypeptide in the test cell is different than the location of KIF18A polypeptide in the control cell, or both (i) and (ii), indicates that the activity of the KIF18A polypeptide in the test cell is different than the activity of a KIF18A polypeptide in the control cell. In this method, the spindle or astral microtubule in the dividing test cell can be banana-shaped, and the spindle or astral microtubule can be detected using an anti-α tubulin antibody and immunocytochemistry.

Methods for assaying for modulation of expression of a KIF18A nucleic acid include a) providing a test cell containing a KIF18A nucleic acid and a control cell containing a KIF18A nucleic acid; and (b) determining a level of an RNA encoded by the KIF18A nucleic acid in the test cell and in the control cell; wherein an increase or decrease in the level of RNA encoded by the KIF18A nucleic acid in the test cell compared to the level of RNA encoded by the KIF18A nucleic acid in the control cell indicates that the expression of a KIF18A nucleic acid is modulated. For example, the level of RNA can be monitored by Northern blot, RT-PCR, or microarray analysis, and the methods can further include determining whether the KIF18A nucleic acid from the test cell contains a mutation.

In another aspect, the invention features methods for assaying for modulation of expression of a KIF18A nucleic acid by a) providing a test cell containing a KIF18A nucleic acid and a control cell containing a KIF18A nucleic acid; and b) determining a level of a KIF18A polypeptide encoded by the KIF18A nucleic acid in the test cell and in the control cell; wherein an increase or decrease in the level of KIF18A polypeptide encoded by the KIF18A nucleic acid in the test cell compared to the level of polypeptide encoded by the KIF18A nucleic acid in the control cell indicates that expression of the KIF18A nucleic acid is modulated. For example, the level of KIF18A polypeptide in the test cell and in the control cell can be determined by Western blot or ELISA, and the methods can further include determining whether the KIF18A nucleic acid in the test cell contains a mutation.

The invention also features methods for modulating the activity of a KIF18A polypeptide or a KLP67A polypeptide by a) contacting a KIF18A nucleic acid or KLP67A nucleic acid with a modulating agent in a concentration sufficient to modulate transcription of the nucleic acid; b) contacting a cell expressing a KIF18A nucleic acid or KLP67A nucleic acid with a modulating agent in a concentration sufficient to modulate translation from an RNA encoded by the nucleic acid; or c) contacting a cell expressing the KIF18A polypeptide or KLP67A polypeptide with a compound that binds to the polypeptide in a concentration sufficient to modulate the activity of the polypeptide. In these methods, the modulating agent can be an antisense nucleic acid molecule, a small inhibitory RNA (siRNA), a ribozyme, a triple helix molecule, an antibody, a small inorganic molecule, or a small non-nucleic acid organic molecule.

In another aspect, the invention includes compositions including a compound that modulates the activity of a KIF18A polypeptide, wherein the composition comprises an antisense nucleic acid molecule, an siRNA, a ribozyme, a triple helix molecule, an antibody, a small inorganic molecule, or a small non-nucleic acid organic molecule. For example, the antisense nucleic acid molecule can be complementary to a segment of contiguous nucleotides of a KIF18A nucleotide sequence ranging from a length of 10 to 1000 nucleotides, and the siRNA can include the sequence of SEQ ID NO:14, or a fragment thereof. The antibody or small molecule can specifically bind to a KIF18A polypeptide, or a fragment or an allelic variant thereof.

The invention also includes kits that include the new compositions and instructions to treat a disorder mediated by or associated with a KIF18A polypeptide, such as proliferative disorders, such as cancer or psoriasis, or autoimmune disorders, e.g., rheumatoid arthritis.

"Compounds" or "agents" described herein can modulate the expression or activity of a mammalian KIF18A or *Drosophila* KLP67A nucleic acid or polypeptide. The new compounds can be, e.g., polypeptides, peptidomimetics, peptoids, small inorganic molecules, small non-nucleic acid organic molecules, and nucleic acid molecules, such as antisense nucleic acid, siRNAs, ribozymes, or triple helix nucleic acids. A "test compound" refers to a compound used in an assay, such as a screening assay, to determine whether or not the compound can modulate KIF18A or KLP67A expression or activity. A test compound that is found to affect KIF18A or KLP67A expression or activity is called a "candidate compound." For example, a compound that disrupts spindle formation in a mitotic cell would be a candidate compound. A therapeutic agent can be identified by an assay (e.g., an in vivo assay) that tests a "candidate compound." In other words, a test compound can be a candidate compound, which can be a therapeutic agent.

The test compound (or candidate compound or therapeutic agent) can be an antisense nucleic acid molecule, a small inhibitory RNA (siRNA), a ribozyme, a triple helix molecule, an antibody, a polypeptide, a peptoid, a polypeptide mimetic, a small inorganic molecule, or a small non-nucleic acid organic molecule.

A KIF18A or KLP67A polypeptide can be localized by immunocytochemistry. Alternatively, or in addition, the polypeptide can be fused to a reporter polypeptide, such as green fluorescent protein (GFP), β-glucuronidase (GUS), luciferase, chloramphenicol transacetylase (CAT), horseradish peroxidase (HRP), or β-galactosidase, and the polypeptide can be localized by the activity of the reporter molecule. In an immunocytochemical technique, a first antibody, which binds the KIF18A or KLP67A polypeptide, can be labeled. Alternatively, a labeled second antibody (an anti-IgG) can be directed against the first (the primary) antibody. This second antibody can be conjugated with a fluorochrome, an enzyme that can produce a colorimetric reaction, or gold beads (for electron microscopy) so that the location of the primary antibody, and thus the antigen, can be recognized.

New isolated antibodies that specifically bind to KIF18A polypeptides or fragments thereof are also described. For example, the KIF18A polypeptide can have the amino acid sequence of SEQ ID NO:2 (FIG. 17), or an allelic variant or fragment thereof. For example, the polypeptide or fragment can consist of amino acid residues 492-507, 492-517, 616-631, 660-667, 730-768, 776-797, or 360-898 of SEQ ID NO:2.

A polynucleotide or polypeptide that is substantially identical in sequence to a human KIF18A cDNA (SEQ ID NO:1) (FIG. 16) or polypeptide sequence (SEQ ID NO:2) (FIG. 17) is at least 80% identical to SEQ ID NO:1 or SEQ ID NO:2. For example, a target DNA or RNA sequence can be 80%, 85%, 95%, or 100% identical to SEQ ID NO:1. A fragment of a target nucleotide sequence (e.g., a sequence that encodes an exon) can be at least 80% identical to a fragment of SEQ ID NO:1.

The invention also features methods of treating a subject having a proliferative disorder associated with aberrant KIF18Apolypeptide expression or activity. One such method includes administering to the subject a therapeutically effective amount of a compound that modulates expression or activity of a KIF18A polypeptide. For example, the compound can be an antisense nucleic acid molecule, an siRNA, a ribozyme, a triple helix molecule, an antibody, a small inorganic molecule, or a small non-nucleic acid organic molecule. The compound can be provided in a kit, which can include instructions for use.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF DRAWINGS

FIG. 16 is the nucleotide sequence of a human KIF18A cDNA (SEQ ID NO:1) (GenBank Accession No. AL136819).

FIG. 17 is the amino acid sequence of a human KIF18A polypeptide (SEQ ID NO:2) (GenBank Accession No. AL136819).

FIG. 18 is the amino acid sequence of a KLP67A polypeptide (SEQ ID NO:3) from *Drosophila melanogaster* (GenBank Accession No. NM_079268).

FIG. 19 is the nucleotide sequence of a KLP67A cDNA (SEQ ID NO:4) from *Drosophila melanogaster* (GenBank Accession No. NM_079268).

FIG. 20 is the nucleotide sequence of a dsRNA targeting KLP61F nucleic acid (SEQ ID NO:13) in *Drosophila melanogaster*.

FIG. 21 is the nucleotide sequence of a dsRNA targeting KLP67A nucleic acid (SEQ ID NO:14) in *Drosophila melanogaster*.

DETAILED DESCRIPTION

Figure 1:
FIG. 1 is a photomicrograph of a primary spermatocyte isolated from the testes of wildtype *Drosophila*, and stained for α-tubulin, centrosomin, and DNA. The spermatocyte is in the prometaphase I stage of meiosis. The image shows two well-separated prominent asters closely apposed to the nuclear envelope.
Figure 2:
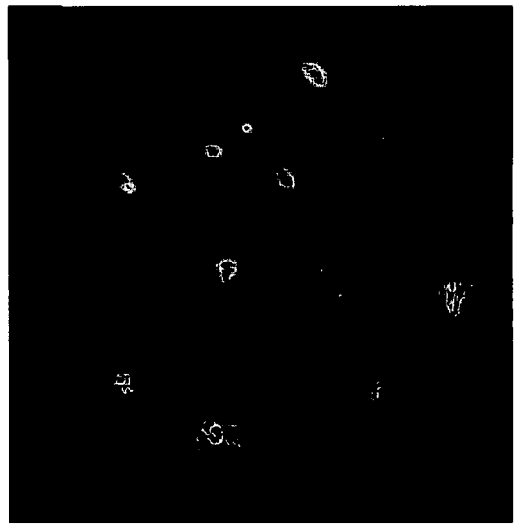
FIG. 2 is a photomicrograph showing two prophase I spermatocytes from the testes of *Drosophila* Df(3L)29A6/KLP67A$^{322b24}$ mutants and stained for α-tubulin, centrosomin, and DNA. The asters are ectopically positioned near one another and disassociated from the nuclear envelope.
Figure 3:
FIG. 3 is a photomicrograph showing a prophase I spermatocyte from the testes of the *Drosophila* Df(3L)29A6/KLP67A$^{322b24}$ mutant and stained for α-tubulin, centrosomin, and DNA. The bulk of one of the centrosomes and its associated aster are detached from the spindle pole.
Figure 4:
FIG. 4 is a photomicrograph showing a tetraploid spermatocyte from the testes of the *Drosophila* Df(3L)29A6/KLP67A$^{322b24}$ mutant and stained for α-tubulin, centrosomin, and DNA. The mutant spermatocyte has four ectopically positioned asters, indicative of failed cytokinesis in a previous gonial division.

The invention relates to compounds that can modulate cell proliferation, and to methods of identifying and using such compounds. Compounds capable of modulating cell proliferation can be useful for treating a subject having a proliferative disorder such as cancer. The subject can be an animal, such as a mammal, or a human. Generally, the methods and compounds target the activity of the kinesin-like protein KIF18A and homologs thereof, and a gene encoding KIF18A or a substantially identical gene. Cell division can be modulated by altering the expression or activity of a KIF18A gene or a KIF18A polypeptide. More specifically, the proper assembly, stabilization, and function of the spindle during mitosis is modulated, e.g., inhibited or enhanced, to inhibit or enhance the process of cell division in specific cells.

KIF18A is a "kinesin superfamily" (KIF) protein. Members of the KIF protein family are known to participate in chromosomal and spindle movements during mitosis and meiosis (Hirokawa et al., *Curr. Opin. Cell Biol.*, 10:60-73, 1998; Vale and Fletterick, *Annu. Rev. Cell Dev. Biol.*, 13:745-777, 1997; Sharp et al., *Nature*, 407:41-47, 2000). The term homolog can refer to a nucleic acid variant of KIF18A. An orthologous gene is related by phylogenetic descent but is found in a different organism. Orthologous genes share functional homology, although not necessarily a strong sequence homology. The amino acid sequences that define the motor domains of human KIF18A and *Drosophila* KLP67A are 52% identical and 69% similar. Thus, as defined herein, a KIF18A ortholog can have an amino acid sequence that defines a functional domain, e.g., a motor domain or a cargo domain, that is at least 65% similar, 67% similar, or 69% similar to the corresponding KIF18A sequence.

The methods and compounds described herein can target the activity of a nucleic acid, e.g., a DNA or mRNA having the sequence of SEQ ID NO:1 (the nucleotide sequence of the human KIF18A cDNA) (FIG. 16) or any substantially identical sequence or any fragment thereof. For example, a composition can target a nucleic acid, such as a gene, that encodes a cDNA substantially identical to SEQ ID NO:1 (FIG. 16). A target DNA sequence can be a variant nucleic acid that differs from the wildtype sequence. Variants can be naturally occurring, such as allelic variants (i.e., variants located at the same genetic locus); substantially identical sequences, such as those that occur at different loci; and orthologs. Alternatively, variants can be non-naturally occurring. Non-naturally occurring variants can be made by mutagenesis techniques, including those applied to polynucleotides, cells, or organisms. Variants can contain nucleotide substitutions, deletions, inversions and/or insertions. Variation can occur in either or both the coding and non-coding regions. A variant nucleotide sequence can encode a conservative or non-conservative amino acid substitution (as compared to the wildtype encoded product). By its sequence similarity, particularly in the motor domain, and its similar intracellular localization pattern as described herein, the *Drosophila* gene KLP67A is an ortholog of human KIF18A. Thus, the methods and compounds described herein can target the activity of a nucleotide or polypeptide sequence of KLP67A. For example, the methods can target a nucleotide sequence consisting of SEQ ID NO:4 (FIG. 19) or an amino acid sequence consisting of SEQ ID NO:3 (FIG. 24). Variants of KIF18A are referred to herein as KIF18A-related polypeptides or nucleic acids.

To determine the percent identity of two amino acid sequences, or two nucleotide sequences, the sequences can be aligned for optimal comparison purposes. For example, gaps can be introduced in one or both of a first and a second amino acid or nucleotide sequence for optimal alignment and non-homologous sequences can be disregarded for comparison purposes. The length of a reference sequence aligned for comparison purposes can be at least 30%, preferably at least 40%, more preferably at least 50%, even more preferably at least 60%, and even more preferably at least 70%, 80%, 90%, or 100% of the length of the reference sequence. For example, when aligning a second sequence to the KIF18A amino acid sequence of SEQ ID NO:2 (FIG. 17) having 899 amino acid residues, at least 270, preferably at least 360, more 20 preferably at least 450, even more preferably at least 540, and even more preferably at least 630, 720, or 810 amino acid residues are aligned. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The determination of percent identity between two amino acid sequences can be accomplished using the BLAST 2.0 program (Gish, W., personal communication). Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (*Nucleic Acids Res.*, 25:3389-3402, 1997).

The methods and compounds can target a polypeptide having the amino acid sequence of SEQ ID NO:2 (FIG. 17), which is the amino acid sequence of the human KIF18A polypeptide, any substantially identical sequence, or any fragment thereof.

The compounds used to modulate KIF18A expression or activity can be one or more of an siRNA, antisense nucleic acid molecule, ribozyme, triple helix molecule, antibody, or small molecule. For example, an siRNA, antisense nucleic acid molecule, or ribozyme targeted to a KIF18A RNA can promote the degradation of an RNA expressed from a gene having the sequence of SEQ ID NO:1 (FIG. 16) or a substantially identical sequence. A triple helix molecule can be used to inhibit expression of a KIF18A target gene by interacting with DNA. An antibody or small molecule that can interact with a KIF18A polypeptide (e.g., SEQ ID NO:2 (FIG. 17), or a substantially identical sequence or fragment thereof) can be used to modulate polypeptide activity, such as to inhibit or increase activity. If KIF18A expression or activity is down regulated as a result of contact with one of the described compounds, spindle assembly and function during mitosis can be inhibited. Cell division would therefore be inhibited, completely or partially.

According to one method described herein, a nucleic acid molecule that encodes and expresses a wildtype or modified (e.g., engineered) KIF18A polypeptide can be introduced into cell that contains a mutant allele of a KIF18A nucleic acid. The nucleic acid molecule can be introduced into the cell via a gene therapy method.

Screening Assays

Methods are described for identifying compounds (e.g., polypeptides, peptidomimetics, peptoids, small inorganic molecules, small non-nucleic acid organic molecules, nucleic acid molecules such as antisense nucleic acids, siRNAs, ribozymes, or triple helix molecules, or other drugs) that modulate KIF18A gene expression or protein activity, or expression or activity of a KIF18A ortholog, such as *Drosophila* KLP67A. These methods are also referred to herein as "screening assays." Compounds thus identified can have a stimulatory or inhibitory effect on KIF18A expression or activity, or can have a stimulatory or inhibitory effect on the expression or activity of a KIF18A substrate. The compounds can be used to modulate the expression or activity of KIF18A or disrupt normal KIF18A interactions. Compounds that affect KIF18A expression or activity can be useful in therapeutic protocols, such as to inhibit undesirable cellular proliferation as occurs, for example, in cancer or psoriasis. Methods described herein can also be used to identify modulators that bind to or alter the activity of a *Drosophila* KLP67A polypeptide or nucleic acid. A compound that can modulate expression or activity of a KIF18A gene or polypeptide or a KLP67A gene or polypeptide is referred to as a modulating agent.

Assays for screening candidate or test compounds that bind to and/or modulate the activity of a KIF18A polypeptide or a biologically active portion thereof are also described. In such assays, the KIF18A polypeptide typically has a motor domain and/or cargo domain. For example, the KIF18A motor domain is from about amino acids 8-283 of SEQ ID NO:2 (FIG. 17).

The test compounds used in the screening assays described herein can be obtained using any of the numerous approaches in combinatorial library methods known in the art, including but not limited to: biological libraries; peptoid libraries (libraries of molecules having the functionalities of polypeptides, but with a novel, non-polypeptide backbone which are resistant to enzymatic degradation but which nevertheless remain bioactive; see, e.g., Zuckermann et al., *J. Med. Chem.*, 37:2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to polypeptide libraries, while the other four approaches are applicable to polypeptide, non-polypeptide oligomer or small molecule libraries of compounds (Lam, *Anticancer Drug Des.*, 12:145, 1997).

Examples of methods for the synthesis of molecular libraries can be found in the art. For example, see DeWitt et al., *Proc. Natl. Acad. Sci. USA*, 90:6909, 1993; Erb et al., *Proc. Natl. Acad. Sci. USA*, 91:11422, 1994; Zuckermann et al., *J. Med. Chem.*, 37:2678, 1994; Cho et al., *Science*, 261:1303, 1993; Carrell et al., *Angew. Chem. Int. Ed. Engl.*, 33:2059, 1994; Carell et al., *Angew. Chem. Int. Ed. Engl.*, 33:2061, 1994; and Gallop et al., *J. Med. Chem.*, 37:1233, 1994.

Libraries of compounds can be presented in solution (e.g., Houghten, *Biotechniques*, 13:412-421, 1992), or on beads (Lam, *Nature*, 354:82-84, 1991), chips (Fodor, *Nature*, 364: 555-556, 1993), bacteria or spores (Ladner, U.S. Pat. No. 5,223,409), plasmids (Cull et al., *Proc. Natl. Acad. Sci., USA*, 89:1865-1869, 1992) or on phage (Scott and Smith, *Science*, 24:386-390, 1990; Devlin, *Science*, 249:404-406, 1990; Cwirla et al., *Proc. Natl. Acad. Sci., USA*, 87:6378-6382, 1990; Felici, *J. Mol. Biol.*, 222:301-310,1991; and Ladner, supra).

An assay can be, for example, a cell-based assay in which a cell that expresses a KIF18A polypeptide or biologically active portion thereof is contacted with a test compound. The contact is typically maintained for the time necessary for an untreated cell to progress through at least one cell cycle. The ability of the test compound to modulate KIF18A expression or activity is then determined. Examples of tests for KIF18A expression or activity are described below. The cell, for example, can be of mammalian origin, such as from human, mouse, rat, hamster, or monkey.

KIF18A localization assays can be employed to evaluate altered KIF18A function in the presence of a test compound. Under wildtype conditions, KIF18A localizes to the distal ends of the astral microtubules and extends into the growth cone of interphase cells. Localization can be achieved, for example, by using immunocytochemistry with antibodies that specifically bind to a KIF18A polypeptide, or by transfecting a cell with a reporter gene fused to a sequence encoding a KIF18A polypeptide. Exemplary reporter genes include green fluorescent protein (GFP), β-glucuronidase (GUS), luciferase, chloramphenicol transacetylase (CAT), horseradish peroxidase (HRP), and β-galactosidase. Methods of producing such fusion polypeptides are known in the art.

To perform a localization assay, a transfected cell can be incubated under conditions appropriate for expression of a KIF18A fusion gene. For example, to assay a test compound, the cell can be contacted with the test compound, and localization of the fusion polypeptide in the presence and absence of the test compound can be determined. An altered localization of the fusion polypeptide in the presence of the test compound indicates that the test compound modulates KIF18A expression or activity either directly or indirectly. In such assays, it is also generally necessary to demonstrate that the fusion polypeptide co-localizes with wildtype KIF18A.

The ability of the test compound to modulate KIF18A expression or activity can also be assayed by monitoring spindle assembly during mitosis of a test cell, such as by fluorescence microscopy. The architecture of the mitotic spindle is indicative of additional, often more subtle, cellular phenotypes caused by modulation of KIF18A activity. For example, inhibition of KIF18A can result in decreased microtubule depolymerization and consequently to increased microtubule length during mitosis and meiosis (see Examples 3 and 4; compare FIGS. 6 and 7, and 8 and 9). Conversely, KIF18A hyperactivity can lead to increased microtubule depolymerization. Altered rates of microtubule depolymerization are manifested by modifications in the length of the mitotic spindle. For example, a decreased rate of microtubule depolymerization can lead to an increase in spindle length by 45-200%, typically 50-100%. Methods to monitor spindle morphology are described below and are known in the art.

Inhibition of KIF18A can result in a variety of other subcellular phenotypes including perturbations in centrosome separation, chromosome segregation and central spindle assembly, which all affect cell division. The presence of two daughter nuclei of different sizes can be an indication of aberrant chromosome segregation (see Example 3). KIF18A deficient cells also exhibit abnormally curved microtubules. The spindles of cells in which KIF18A activity is inhibited are generally curved in appearance, e.g., banana-shaped (see Example 4, compare FIGS. 12 and 13). Thus, introduction of a test compound into a cell culture, and incubation for a suitable period of time (such as the time required for at least one cell cycle in the absence of the test compound), followed by fixation and detection of microtubules can be used to confirm whether a test compound that affects KIF18A can affect cell division.

Another phenotype attributed to KIF18A inhibition is the ectopic localization of prophase centrosomes in the cytoplasm, e.g., at an angle less than 155.0° from each other, such as at an angle ranging from 1-155°, from 20-155°, from 100-155°, or 130-154° from each other. During normal cell division, cells are typically located further apart, ranging from 155°-180° apart (e.g., from 160°-170° apart) (see Example 4, FIGS. 12 and 13). Centrosomes and their associated asters can also appear to detach from the spindle poles, giving rise to asters that freely float in the cytoplasm. The localization of the asters, which mark the centrosomes, can be accomplished by immunocytochemistry experiments that include exposing the cell to an anti-centrosomin antibody. Generally, the timing of centrosome separation is also increased in KIF18A deficient cells. The period of centrosome migration up until the point of nuclear envelope breakdown can be increased by 100-600% (e.g., 200, 300, or 400%).

Cell structure morphologies can be monitored using a combination of immunocytochemistry and specialized stains. For example, cell structure morphology can be assayed by labeling with anti-α tubulin (Sigma; St. Louis, Mo.), anti-centrosomin, and/or anti-myosin II antibodies. Actin staining, such as with a phalloidin (e.g., rhodamine-phalloidin; Molecular Probes; Eugene, Oreg.) can also be used to examine cell morphology. A fluorescent conjugate of tubulin, such as a tetramethylrhodamine-tubulin; Cytoskeleton Inc., Denver, Colo.) can be injected into cells to generate fluorescent microtubules for assay in vivo.

The ability of a test compound to modulate KIF18A binding to a cellular molecule, such as a microtubule, can also be evaluated. This can be accomplished in vivo or in vitro, for example, by coupling the molecule with a radioisotope or enzymatic label such that binding of the molecule to KIF18A can be determined by detecting the labeled molecule in a complex. For example, molecules can be labeled with $^{125}I$, $^{35}S$, $^{14}C$, or $^3H$, either directly or indirectly, and the radioisotope detected by direct counting of radioemission or by scintillation counting. Alternatively, molecules can be enzymatically labeled with, for example, horseradish peroxidase, alkaline phosphatase, or luciferase, and the enzymatic label detected by determination of conversion of an appropriate substrate, to product.

In one alternative, a cell-free assay can be provided in which a KIF18A polypeptide or biologically active portion thereof is contacted with a test compound and the ability of the test compound to bind to the KIF18A polypeptide or biologically active portion thereof is evaluated. The biologically active portions of the KIF18A polypeptides to be used in assays described herein can include fragments that participate in interactions with non-KIF18A molecules.

KIF18A polypeptides or biologically active portions thereof can be used in the cell-free assays described herein. Cell-free assays involve preparing a reaction mixture of KIF18A and the test compound under conditions and for a time sufficient to allow the two components to interact and bind, thus forming a complex that can be displaced and/or detected.

The interaction between two molecules (e.g., a KIF18A polypeptide or fragment thereof, and a test compound) can also be detected, for example, by using Fluorescence Resonant Energy Transfer (FRET). In this example, a fluorophore label on the first, 'donor' molecule (e.g., a KIF18A polypeptide or biologically active portion) is selected such that its emitted fluorescent energy will be absorbed by a fluorescent label on a second, 'acceptor' molecule (e.g., a test compound), which in turn is able to fluoresce due to the absorbed energy. Alternately, the 'donor' polypeptide molecule can utilize the natural fluorescent energy of tryptophan residues. Labels are chosen that emit different wavelengths of light, such that the 'acceptor' molecule label can be differentiated from that of the 'donor.' Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FRET binding event can be measured through standard fluorometric detection means well known in the art (e.g., using a fluorimeter).

The ability of a KIF18A polypeptide to bind to a target molecule can also be determined using real-time Biomolecular Interaction Analysis (BIA) (see, e.g., Sjolander and Urbaniczky, *Anal. Chem.*, 63:2338-2345, 1991; and Szabo et al., *Curr. Opin. Struct. Biol.*, 5:699-705, 1995). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules. The target molecule can be a test compound. To assay the ability of a test compound to modulate the interaction between KIF18A and a KIF18A substrate such as a microtubule, the incubation mix can contain a KIF18A polypeptide or fragment thereof, a KIF18A substrate, and the test compound. An alteration in the interaction between the KIF18A polypeptide or fragment and the substrate in the presence of the test compound indicates that the test compound is a candidate compound for modulating KIF18A activity.

In one example, a KIF18A polypeptide or a test compound is anchored onto a solid phase. The KIF18A/test compound complexes anchored on the solid phase can be detected at the end of the reaction. For example, KIF18A can be anchored onto a solid surface, and the test compound (which is not anchored) can be labeled, either directly or indirectly, with detectable labels, some of which are discussed herein.

A KIF18A polypeptide, an anti-KIF18A antibody; or a KIF18A target molecule (e.g., a binding partner, such as a microtubule) can be immobilized to facilitate separation of complexed from uncomplexed forms of one or both of the polypeptides, as well as to accommodate automation of the assay. Binding of a test compound to a KIF18A polypeptide, or interaction of a KIF18A polypeptide with a target molecule in the presence and absence of a test compound, can be accomplished in any vessel suitable for containing the reactants. Examples of such vessels include microtiter plates, test tubes, and micro-centrifuge tubes. In one embodiment, a fusion polypeptide can be provided that adds a domain that allows one or both of the polypeptides to be bound to a matrix. For example, a glutathione-S-transferase/KIF18A fusion polypeptides or glutathione-S-transferase/target fusion polypeptides can be adsorbed onto glutathione sepharose beads (Sigma Chemical, St. Louis, Mo.) or glutathione derivatized microtiter plates, which are then combined with the test compound, or the test compound and either the non-adsorbed target polypeptide or KIF18A polypeptide, and the mixture incubated under conditions conducive to complex formation (e.g., at physiological conditions for salt and pH).

Following incubation, the beads or microtiter plate wells can be washed to remove any unbound components, the matrix immobilized in the case of beads, and the complex assayed either directly or indirectly, for example, as described above. Alternatively, the complexes can be dissociated from the matrix and the level of KIF18A binding or activity determined using methods known in the art.

Other techniques for immobilizing either a KIF18A polypeptide or a target molecule on. matrices include using conjugation of biotin and streptavidin. Biotinylated KIF18A polypeptide or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). To conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface, such as by using a labeled antibody-specific for the non-immobilized component (the antibody, in turn, can be directly labeled or indirectly labeled with, for example, a labeled anti-Ig antibody). To assay the ability of a test compound to bind to a KIF18A polypeptide or fragment thereof, either the test compound or the KIF18A polypeptide or fragment can be the immobilized component. The components can be, for example, a KIF18A polypeptide or fragment thereof, and a KIF18A substrate, such as a microtubule. The assay can be performed by comparing binding of the KIF18A polypeptide or fragment to the substrate in the presence and absence of the test compound. An alteration in the amount of binding in the presence of the test compound indicates that the test compound is a candidate compound for modulating KIF18A activity.

The assay can be performed by utilizing antibodies that specifically bind to KIF18A polypeptide or target molecules, but that do not interfere with binding of the KIF18A polypeptide to its target molecule (e.g., the microtubule). Such antibodies can be derivatized to the wells of the plate, and unbound target or KIF18A polypeptide can be trapped in the wells by antibody conjugation. Methods for detecting such complexes, in addition to those described above for the GST-immobilized complexes, include immunodetection of complexes using antibodies reactive with the KIF18A polypeptide or target molecule, as well as enzyme-linked assays that rely on detecting an enzymatic activity associated with the KIF18A polypeptide or target molecule.

Cell free assays can be conducted in a liquid phase. In such an assay, the reaction products are separated from unreacted components by any of a number of standard techniques, including but not limited to: differential centrifugation (see, for example, Rivas, G., and Minton, A. P., Trends Biochem Sci., 18:284-7, 1993); chromatography (gel filtration chromatography, ion-exchange chromatography); electrophoresis (see, e.g., Ausubel et al., eds. *Current Protocols in Molecular Biology* 1999, J. Wiley: New York.); and immunoprecipitation (see, for example, Ausubel et al., supra). Such resins and chromatographic techniques are known to one skilled in the art (see, e.g., Heegaard, *J. Mol. Recognit.* 11:141-8, 1998; Hage and Tweed, *J. Chromatogr. B. Biomed. Sci. Appl.* 699: 499-525, 1997). Further, fluorescence energy transfer can also be conveniently utilized, as described herein, to detect binding without further purification of the complex from solution.

A cell-free assay can include contacting the KIF18A polypeptide or biologically active portion thereof with a known compound which binds KIF18A to form an assay mixture, contacting the assay mixture with a test compound, and determining the ability of the test compound to interact with a KIF18A polypeptide, wherein determining the ability of the test compound to interact with a KIF18A polypeptide includes determining the ability of the test compound to preferentially bind to KIF18A or biologically active portion thereof, or to modulate the activity of a target molecule, as compared to the known compound.

Compounds that disrupt binding of KIF18A to a cellular molecule (i.e., a binding partner), such as a microtubule, can be useful for regulating the activity of KIF18A. Such compounds can include, but are not limited to antibodies, polypeptides, peptoids, peptidomimetics, small non-nucleic acid organic molecules, and small inorganic molecules. In one alternative, or optionally, the ability of the test compound to modulate the activity of a KIF18A polypeptide can be tested by assay of the activity of a downstream effector of a KIF18A target molecule. For example, the activity of the effector molecule on an appropriate target can be determined, or the binding of the effector to an appropriate target can be determined, as previously described.

To identify compounds that interfere with the interaction between a KIF18A polypeptide, and a cellular binding partner, such as a microtubule, a reaction mixture containing a KIF18A polypeptide and the binding partner is prepared under conditions and for a time sufficient to allow the two products to form a complex. To test an inhibitory compound, the reaction mixture can be provided in the presence and absence of the test compound. The test compound can be initially included in the reaction mixture, or can be added at a time subsequent to the addition of KIF18A and its cellular binding partner. Control reaction mixtures can be incubated without the test compound or with a control solution such as buffer that does not contain the test compound. The formation of complexes between KIF18A and the binding partner can then be detected. The formation of a complex in the control reaction, but not in the reaction mixture containing the test compound, indicates that the compound interferes with the interaction between KIF18A and the binding partner. Alternatively, or in addition, complex formation within reaction mixtures containing the test compound and normal KIF18A can also be compared to complex formation within reaction mixtures containing the test compound and mutant target gene product. This comparison can be important in those cases where it is desirable to identify compounds that disrupt interactions of mutant but not normal KIF18A gene products. In this and all assays described herein, a fragment of a KIF18A polypeptide can be used.

These assays can be conducted in a heterogeneous or homogeneous format. Heterogeneous assays involve anchoring either a KIF18A polypeptide or biologically active fragment thereof, or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between KIF18A and a binding partner, such as by competition, can be identified by conducting the reaction in the presence of the test substance. Alternatively, test compounds that disrupt preformed complexes (e.g., compounds with higher binding constants that displace one of the components from the complex) can be tested by adding the test compound to the reaction mixture after complexes have been formed. The various formats are briefly described below.

In a heterogeneous assay system, either KIF18A or the binding partner can be anchored onto a solid surface, such as a microtiter plate, while the non-anchored species is labeled either directly or indirectly. The anchored species can be immobilized by non-covalent or covalent attachments. Alternatively, an immobilized antibody specific for the species to be anchored can be used to anchor the species to the solid surface.

To conduct the assay, the partner of the immobilized species can be exposed to the coated surface with or without the test compound. After the reaction is complete, unreacted components can be removed (e.g., by washing), and any complexes that have formed will remain immobilized on the solid surface. In assays where the non-immobilized species is pre-labeled, the detection of label immobilized on the surface indicates that complexes were formed. In assays where the non-immobilized species is not pre-labeled, an indirect label can be used to detect complexes anchored on the surface, such as by using a labeled antibody specific for the initially non-immobilized species (the antibody, in turn, can be directly labeled or indirectly labeled with, for example, a labeled anti-Ig antibody). Depending upon the order of addition of reaction components, test compounds that inhibit complex formation or that disrupt preformed complexes can be detected.

Alternatively, or in addition, the reaction can be conducted in a liquid phase in the presence or absence of the test compound. Reaction products can be separated from unreacted components and complexes can be assayed using, for example, a first immobilized antibody specific for one of the binding components to anchor any complexes formed in solution and a second labeled antibody specific for the other partner to detect anchored complexes. This method or a variation thereof can be used to identify compounds that inhibit complex formation or that disrupt preformed complexes.

Other homogeneous assays can also be used. For example, a preformed complex of a KIF18A polypeptide or biologically active portion thereof, and the interactive binding partner product is prepared in which either KIF18A or the binding partner is labeled, but the signal generated by the label is quenched due to complex formation (see, e.g., U.S. Pat. No. 4,109,496 that utilizes this approach for immunoassays). The addition of a compound that competes with and displaces one of the species from the preformed complex will result in the generation of a signal above background. In this way, test substances that disrupt KIF18A-binding partner interaction can be identified.

The KIF18A polypeptides can also be used as "bait proteins," such as in a two-hybrid assay or three-hybrid assay (see, e.g., U.S. Pat. No. 5,283,317; Zervos et al., *Cell*, 72:223-232, 1993; Madura et al., *J. Biol. Chem.*, 268:12046-12054, 1993; Bartel et al., *Biotechniques*, 14:920-924, 1993; Iwabuchi et al., *Oncogene*, 8:1693-1696, 1993; and Brent, WO 94/10300), to identify other polypeptides that bind to or interact with KIF18A ("KIF18A -binding polypeptides" or "KIF18A-bp") and are involved in KIF18A activity. Such KIF18A-bps can be activators or inhibitors of signals by the KIF18A polypeptides or KIF18A targets as, for example, downstream elements of a KIF18A-mediated signaling pathway.

The two-hybrid system is based on the modular nature of most transcription factors, which consist of separable DNA-binding and activation domains. Briefly, the assay utilizes two different DNA constructs. In one construct, a nucleotide sequence that codes for a KIF18A polypeptide or biologically active portion thereof, is fused to a gene encoding the DNA binding domain of a known transcription factor (e.g., GAL4). In the other construct, a DNA sequence from a library of DNA sequences that encodes an unidentified protein ("prey" or "sample") is fused to a nucleotide sequence that codes for the activation domain of the known transcription factor. Alternatively, the KIF18A nucleotide sequence can be fused to the sequence encoding an activator domain. If the "bait" and the "prey" proteins are able to interact in vivo and form a KIF18A-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the KIF18A polypeptide.

The two hybrid system can be used, for example, to identify modulators of KIF18A gene expression. For example, a cell or cell free mixture is contacted with a test compound and the expression of a KIF18A nucleic acid or polypeptide can be evaluated relative to the level of expression of KIF18A in the absence of the test compound. When expression of a KIF18A nucleic acid or polypeptide is greater in the presence of the test compound than in its absence, the candidate compound is identified as a stimulator of KIF18A nucleic acid or polypeptide expression. Alternatively, when expression of KIF18A nucleic acid or polypeptide is less (statistically significantly less) in the presence of the test compound than in its absence, the test compound is identified as an inhibitor of KIF18A nucleic acid or polypeptide expression. The level of KIF18A nucleic acid or polypeptide expression can be determined by methods described herein. For example, quantitation of RNA can be accomplished by Northern blot analysis or quantitative RT-PCR. Microarray analysis can also be used to determine whether RNA levels are increased or decreased as compared to wildtype levels after treatment with a test compound. Polypeptide levels can be monitored and/or quantitated by Western blot or ELISA.

Any two or more of the assays described herein can be performed sequentially or in combination. For example, a modulating agent can be identified using a cell-based or a cell free assay, and the ability of the compound to modulate the activity of a KIF18A polypeptide can be confirmed in vivo, such as in mitotically dividing cell culture.

Compounds identified by the above-described screening assays also relate to the invention described herein. Accordingly, it is within the scope of this invention to further use a compound identified as described herein (e.g., a KIF18A modulating agent, an antisense KIF18A nucleic acid molecule, a KIF18A-specific antibody, or a KIF18A-binding partner) in an appropriate animal model to determine the efficacy, toxicity, side effects, or mechanism of action, of treatment with such a compound. Furthermore, novel compounds identified by the above-described screening assays can be used for treatments as described herein.

The methods described herein can be used to identify modifiers of KIF18A-related polypeptides or nucleic acids, such as *Drosophila* KLP67A polypeptides or nucleic acids. For example, the methods can be used to identify a compound that alters KLP67A activity, thereby identifying a candidate modulator of KIF18A activity. The identified modulator can then be assayed for a direct or indirect effect on KIF18A activity.

Anti-KIF18A Antibodies

Anti-KIF18A antibodies can be made using standard techniques. The term "antibody," as used herein, refers to an immunoglobulin molecule or immunologically active portion thereof (i.e., an antigen-binding portion). Examples of immunologically active portions of immunoglobulin molecules include Fab and F(ab')2 fragments that can be generated by treating the antibody with an enzyme such as pepsin.

The antibody can be a polyclonal, monoclonal, recombinant (e.g., a chimeric or humanized, fully human, non-human, such as murine), or single chain antibody. The antibody can be coupled to a toxin or imaging agent.

An isolated or purified full-length KIF18A polypeptide, or antigenic polypeptide fragment of KIF18A, can be used as an immunogen or can be used to identify anti-KIF18A antibodies made with other immunogens, such as cells, membrane preparations, and the like. Exemplary antigenic polypeptide fragments are defined by amino acid sequence fragments of SEQ ID NO:2 (FIG. 17), including, for example, residues 492-507, 492-517, 616-631, 660-667, 753-768, 776-797, or 360-898. The antigenic polypeptide will preferably encompass a highly charged epitope of KIF18A.

As used herein, an "isolated" or "purified" KIF18A polypeptide or polypeptide fragment is a KIF18A polypeptide or polypeptide fragment that is substantially free of cellular material or other contaminating polypeptides from the cell or tissue source in which the KIF18A polypeptide naturally occurs. A KIF18A polypeptide fragment that is substantially free of cellular material includes preparations of KIF18A polypeptide fragments having less than about 30% (by dry weight) of non-KIF18A polypeptide.

KIF18A polypeptide fusion polypeptides include all or part of a KIF18A sequence fused to sequences derived from a member of the immunoglobulin polypeptide family. The resulting KIF18A-immunoglobulin fusion polypeptide can be used as an immunogen to produce anti-KIF18A antibodies in an animal, to purify KIF18A ligands, and in screening assays to identify molecules that can inhibit the interaction of a KIF18A polypeptide with a substrate, such as a microtubule.

A KIF18A chimeric or fusion polypeptide can be produced by conventional recombinant DNA techniques. For example, DNA fragments coding for the different polypeptide sequences can be ligated together in-frame in accordance with conventional techniques. This can be done using blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al. (eds), *Current Protocols in Molecular Biology*, John Wiley & Sons, 1992). Moreover, many expression vectors are commercially available that already encode a fusion moiety, such as a GST polypeptide. A KIF18A-encoding nucleic acid can be cloned into such an expression vector such that the sequence encoding the fusion moiety is linked in-frame to the sequence encoding the KIF18A polypeptide.

An isolated KIF18A epitope can be used as an immunogen to generate antibodies that bind a KIF18A polypeptide or epitope using standard techniques for polyclonal and monoclonal antibody preparation. Immunogens that include an antigenic polypeptide that includes all or part of a KIF18A amino acid sequence are particularly related to the invention described herein. The antigenic polypeptide of KIF18A consists of at least 8 (preferably 10, 15, 20, or 30) amino acid residues of the amino acid sequence shown in SEQ ID NO:2 (FIG. 17) such that an antibody raised against the polypeptide forms a specific immune complex with a KIF18A polypeptide or polypeptide fragment.

A KIF18A epitope immunogen is used to prepare antibodies by immunizing a suitable animal, such as a rabbit, goat, mouse, or other mammal) with the immunogen. An appropriate immunogenic preparation can contain, for example, recombinantly expressed KIF18A or a chemically synthesized KIF18A polypeptide. The preparation can further include an adjuvant, such as Freund's complete or incomplete adjuvant, or a similar immunostimulatory agent. Immunization with an immunogenic KIF18A epitope preparation induces a polyclonal anti-KIF18A antibody response.

Examples of immunologically active portions of immunoglobulin molecules include Fab and F(ab')2 fragments, which can be generated by treating the antibody with an enzyme such as pepsin. The invention provides polyclonal and monoclonal antibodies that bind KIF18A or a KIF8A polypeptide fragment. The term "monoclonal antibody" or "monoclonal antibody composition," as used herein, refers to a population of antibody molecules that contain only one species of an antigen binding site capable of immunoreacting with a particular epitope of KIF18A. A monoclonal antibody composition thus typically displays a single binding affinity for a particular KIF18A epitope with which it immunoreacts.

Polyclonal KIF18A epitope antibodies can be prepared as described above by immunizing a suitable subject with a KIF18A epitope immunogen. The anti-KIF18A epitope antibody titer in the immunized subject can be monitored over time by standard techniques, such as with an enzyme linked immunosorbent assay (ELISA) using immobilized KIF18A polypeptide or polypeptide fragment. If desired, the antibody molecules directed against a KIF18A polypeptide fragment can be isolated from the mammal (e.g., from the blood) and further purified by well-known techniques, such as protein A chromatography to obtain the IgG fraction. At an appropriate time after immunization, e.g., when the anti-KIF18A antibody titers are highest, antibody-producing cells can be obtained from the subject and used to prepare monoclonal antibodies by standard techniques, such as the hybridoma technique originally described by Kohler and Milstein, *Nature*, 256:495-497, 1975, the human B cell hybridoma technique (Kozbor et al., *Immunol. Today*, 4:72, 1983), the EBV-hybridoma technique (Cole et al., *Monoclonal Antibodies and Cancer Therapy*, Alan R. Liss, Inc., pp. 77-96, 1985) or trioma techniques. The technology for producing various antibodies monoclonal antibody hybridomas is well known (see generally Coligan et al. (eds.) *Current Protocols in Immunology*, John Wiley & Sons, Inc., New York, N.Y., 1994).

Any of the many well known protocols used for fusing lymphocytes and immortalized cell lines can be applied for the purpose of generating a KIF18A epitope monoclonal antibody (see, e.g., Coligan et al., supra; Galfre et al., *Nature*, 266:55052,1977; Kenneth, in *Monoclonal Antibodies: A New Dimension In Biological Analyses*, Plenum Publishing Corp., New York, N.Y., 1980; and Lerner, *J. Biol. Med.*, 54:387-402, 1981). Moreover, the ordinarily skilled worker will appreciate that there are many variations of such methods that also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a KIF18A epitope, e.g., using a conventional ELISA assay.

Alternative to preparing monoclonal antibody-secreting hybridomas, a monoclonal anti-KIF18A antibody can be identified and isolated by screening a recombinant combinatorial immunoglobulin library (e.g., an antibody phage display library) with a KIF18A polypeptide or polypeptide fragment to thereby isolate immunoglobulin library members that bind a KIF18A polypeptide epitope. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology*, 9:1370-1372, 1991; Hay et al., *Hum. Antibod. Hybridomas*, 3:81-85, 1992; Huse et al., *Science*, 246: 1275-1281, 1989; Griffiths et al., *EMBO J.*, 12:725-734, 1993.

Additionally, recombinant anti-KIF18A antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., *Science*, 240:1041-1043, 1988; Liu et al., *Proc. Natl. Acad. Sci. USA*, 84:3439-3443, 1987; Liu et al., *J. Immunol.*, 139:3521-3526, 1987; Sun et al., *Proc. Natl. Acad. Sci. USA*, 84:214-218, 1987; Nishimura et al., *Canc. Res.*, 47:999-1005, 1987; Wood et al., *Nature*, 314:446-449, 1985; and Shaw et al., *J. Natl. Cancer Inst.*, 80:1553-1559, 1988; Morrison, *Science*, 229:1202-1207, 1985; Oi et al., *Bio/Techniques*, 4:214, 1986; U.S. Pat. No. 5,225,539; Jones et al., *Nature*, 321:552-525, 1986; Verhoeyan et al., *Science*, 239:1534, 1988; and Beidler et al., *J. Immunol.*, 141:4053-4060, 1988.

An anti-KIF18A antibody (e.g., monoclonal antibody) is useful for isolating a KIF18A polypeptide or polypeptide fragment by standard techniques, such as affinity chromatography or immunoprecipitation. For example, an anti-KIF18A antibody can be used to facilitate the purification of natural KIF18A from cells and of a recombinantly produced KIF18A polypeptide or polypeptide fragment expressed in host cells. Such antibodies are also useful for detecting a KIF18A polypeptide or polypeptide fragment, such as in a cellular lysate or cell supernatant, in order to evaluate the abundance, pattern of expression, and localization of the KIF18A polypeptide or polypeptide fragment. Anti-KIF18A antibodies can be used diagnostically to monitor polypeptide levels in tissue as part of a clinical testing procedure to, for example, determine the efficacy of a given treatment regimen for spinal muscular atrophy. Antibody detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies specific for a KIF18A polypeptide or polypeptide fragment are useful for screening assays as described herein, as commercially available reagents, or for other uses of antibodies that are known in the art.

Diagnostic and Prognostic Assays

The presence, level, or absence of a KIF18A polypeptide or nucleic acid in a biological sample, particularly following treatment with a method and/or pharmaceutical composition of the invention, can be evaluated by obtaining a biological sample from a test subject and contacting the biological sample with a compound or agent capable of detecting a KIF18A polypeptide or nucleic acid (e.g., mRNA or genomic DNA) such that the presence of a KIF18A polypeptide or nucleic acid is detected in the biological sample. "Biological samples" include tissues, cells, and biological fluids isolated from a subject, as well as tissues, cells, and fluids present within a subject. The level of expression of the KIF18A gene can be measured in a number of ways, including, but not limited to: measuring the mRNA encoded by the KIF18A gene; measuring the amount of polypeptide encoded by the KIF18A gene; or measuring the activity of the polypeptide encoded by the KIF18A gene.

The level of mRNA corresponding to the KIF18A gene in a cell can be determined using any suitable protocol, in situ or in vitro.

An isolated mRNA can be used in hybridization or amplification assays that include, but are not limited to, Northern blot analyses, polymerase chain reaction analyses, and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length KIF18A nucleic acid, such as the nucleic acid of SEQ ID NO:1 (FIG. 16), or an oligonucleotide of at least 7, 15, 30, 50, 100, 250, or 500 nucleotides in length and sufficient to specifically hybridize under stringent conditions to KIF18A mRNA or genomic DNA. Other suitable probes for use in the diagnostic assays are described herein.

In one format, mRNA (or cDNA) is immobilized on a surface and contacted with the probe. For example, the isolated mRNA can be separated on an agarose gel and transferred to a membrane, such as nitrocellulose. In an alternative format, the probes are immobilized on a surface and the mRNA (or cDNA) is contacted with the probes, such as in a two-dimensional gene chip array. A skilled artisan can adapt known mRNA detection methods for use in detecting the level of mRNA expressed by a KIF18A gene.

The level of mRNA in a sample that is encoded by a KIF18A nucleic acid can be evaluated with nucleic acid amplification, such as by RT-PCR (Mullis, 1987, U.S. Pat. No. 4,683,202), ligase chain reaction (Barany, Proc. Natl. Acad. Sci. USA, 88:189-193, 1991), self-sustained sequence replication (Guatelli et al., *Proc. Natl. Acad. Sci. USA*, 87:1874-1878, 1990), transcriptional amplification system (Kwoh et al., *Proc. Natl. Acad. Sci. USA*, 86:1173-1177, 1989), Q-Beta Replicase (Lizardi et al., *Bio/Technology*, 6:1197, 1988), rolling circle replication (Lizardi et al., U.S. Pat. No. 5,854,033), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and that contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the KIF18A gene being analyzed.

In another embodiment, the in situ methods further consist of contacting a control sample with a compound or agent capable of detecting KIF18A mRNA, or genomic DNA, and comparing the presence of KIF18A mRNA or genomic DNA in the control sample with the presence of KIF18A mRNA or genomic DNA in the test sample.

A variety of methods can be used to determine the level of protein encoded by KIF18A. In general, these methods include contacting an agent that selectively binds to the protein, such as an antibody, with a sample, to evaluate the level of protein in the sample. The antibody can optionally be conjugated to a detectable label. Antibodies can be polyclonal or monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect KIF18A polypeptide in a biological sample in vitro as well as in vivo. In vitro techniques for detection of KIF18A polypeptide include enzyme linked immunosorbent assays (ELISAs), immunoprecipitations, immunofluorescence, enzyme immunoassays (EIA), radioimmunoassays (RIA), and Western blot analysis. In vivo techniques for detection of a KIF18A polypeptide include introducing into a subject a labeled anti-KIF18A antibody. For example, the antibody can be labeled with a radioactive marker whose presence and location in a subject can be detected by standard imaging techniques.

In an alternative method, the control sample and the test sample can be contacted with a compound or agent capable of detecting a KIF18A polypeptide. The presence (e.g., amount) of KIF18A polypeptide in the control sample can be compared to the presence (e.g., amount) of KIF18A polypeptide in the test sample.

The invention also includes kits for detecting the presence of a KIF18A polypeptide or nucleic acid in a biological sample. The kits can include (1) a compound or agent capable of detecting a KIF18A polypeptide or nucleic acid in a biological sample, and (2) a standard. The compound or agent can be packaged in a suitable container. The kits can further include instructions for using the kit to detect a KIF18A polypeptide or nucleic acid.

For antibody-based kits, the kits can include: (1) a first antibody (e.g., attached to a solid support) which binds to a KIF18A polypeptide, and, optionally, (2) a second antibody that binds to either the polypeptide or to the first antibody and is conjugated to a detectable agent.

For oligonucleotide-based kits, the kits can include: (1) an oligonucleotide (e.g., a detectably labeled oligonucleotide) that hybridizes to a nucleotide sequence encoding a KIF18A polypeptide or (2) a pair of primers useful for amplifying a KIF18A nucleic acid molecule.

The kits described herein can include a buffering agent, a preservative, or a polypeptide stabilizing agent. The kits can also include components necessary for detecting the detectable agent (e.g., an enzyme or a substrate), and/or a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted KIF18A expression or activity. "Unwanted" expression or acticity can cause pain or deregulated cell proliferation. A disease or disorder associated with misexpressed or aberrant or unwanted KIF18A expression or activity can be a proliferative disorder. A proliferative disorder is a disorder characterized by irregularities in cell division, such as a cancer, psoriasis, or atopic dermatitis. For example, a cancer can be a melanoma, prostate cancer, cervical cancer, breast cancer, colon cancer, or sarcoma. The cancer can be a leukemia. The diagnostic methods described herein can be used to identify a tumor cell, hyperproliferative cell, or neoplastic cell, which all have the capacity for autonomous growth, i.e., an abnormal state or condition characterized by rapidly proliferating cell growth. The methods can be used to detect cancerous growths or oncogenic processes, or metastatic tissues or malignantly transformed cells, tissues, or organs, irrespective of histopathologic type or stage of invasiveness. The methods can be used to detect malignancies in any organ system, including, but not limited to, the lung, breast, thyroid, lymphoid, gastrointestinal, and genito-urinary tract. The methods can also be used to detect adenocarcinomas, which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, which can include, for example, malignant tumors composed of carcinomatous and sarcomatous tissues.

A disease or disorder associated with misexpressed or aberrant or unwanted KIF18A expression or activity can be an autoimmune disorder, such as rheumatoid arthritis. Thus, the diagnostic methods described herein can identify subjects having, or at risk for developing, an autoimmune disorder. Other rheumatic diseases that can be associated with aberrant or unwanted KIF18A expression or activity include systemic lupus erythematosus, Sjögren's syndrome, scleroderma, mixed connective tissue disease, dermatomyositis, polymyositis, and Reiter's syndrome. Other autoimmune diseases include autoimmune lymphoproliferative syndrome (ALPS); autoimmune disease of the central nervous system, such as multiple sclerosis, myasthenia gravis, and encephalomyelitis; atopic dermatitis; inflammatory bowel disease (e.g., ulcerative colitis or Crohn's Disease).

Methods relating to the invention can be used to detect a disease or disorder associated with aberrant or unwanted KIF18A expression or activity. For example, according to one method, a test sample can be obtained from a subject, and the KIF18A polypeptide or nucleic acid (e.g., mRNA or genomic DNA) of the sample can be evaluated. For example, the level (e.g., the presence or absence) of KIF18A polypeptide or nucleic acid in the sample can be diagnostic for a subject having or at risk of developing a disease or disorder associated with aberrant or unwanted KIF18A expression or activity. As used herein, a "test sample" refers to a biological sample obtained from a subject of interest, including a biological fluid (e.g., serum), cell sample, or tissue.

The prognostic assays described herein can be used to determine whether a subject can be administered a compound (e.g., an agonist, antagonist, peptidomimetic, protein, polypeptide, nucleic acid, small molecule, or other drug candidate) to treat a disease or disorder associated with aberrant or unwanted KIF18A expression or activity. For example, such methods can be used to determine whether a compound can be administered to a subject to effectively treat a cell proliferation disorder.

The methods described herein can be used to detect genetic alterations in a KIF18A gene, thereby determining if a subject with the altered gene is at risk for a disorder characterized by misregulation in KIF18A protein activity or nucleic acid expression, such as a proliferation disorder. For example, the methods include detecting, in a sample from the subject, the presence or absence of a genetic alteration characterized by at least one of an alteration affecting the integrity of a gene encoding a KIF18A protein, or the mis-expression of the KIF18A gene. For example, such genetic alterations can be detected by ascertaining the existence of at least one of the following: 1) a deletion of one or more nucleotides from a KIF18A gene; 2) an addition of one or more nucleotides to a KIF18A gene; 3) substitution of one or more nucleotides in a KIF18A gene; 4) a chromosomal rearrangement of a KIF18A gene; 5) an alteration in the level of a messenger RNA transcript of a KIF18A gene; 6) aberrant modification of a KIF18A gene, such as the methylation pattern of the genomic DNA; 7) the presence of a non-wildtype splicing pattern of a messenger RNA transcript of a KIF18A gene; 8) a non-wildtype level of a KIF18A protein; 9) allelic loss of a KIF18A gene; and 10) inappropriate post-translational modification of a KIF18A protein.

A genetic alteration can be detected with a probe/primer in a polymerase chain reaction, such as anchor PCR or RACE PCR, or, alternatively, in a ligation chain reaction (LCR), the latter of which can be particularly useful for detecting point mutations in the KIF18A gene. This method can include the steps of collecting a sample of cells from a subject, isolating nucleic acid (e.g., genomic, mRNA or both) from the sample, contacting the nucleic acid sample with one or more primers that specifically hybridize to a KIF18A gene under conditions such that hybridization and amplification of the KIF18A gene (if present) occurs, and detecting the presence or absence of an amplification product or detecting the size of the amplification product and comparing the length to a control sample. PCR and/or LCR may be desirable to use as a preliminary amplification step in conjunction with any of the techniques used for detecting mutations described herein. Alternative amplification methods are described above and can be used in a preliminary amplification step, followed by the detection of the amplified molecules using techniques known to those of skill in the art.

Mutations in a KIF18A gene from a sample cell can be identified by detecting alterations in restriction enzyme cleavage patterns. For example, sample and control DNA can be isolated, amplified (optionally), digested with one or more restriction endonucleases, and fragment length sizes determined, such as by gel electrophoresis, and compared. Differences in fragment length sizes between sample and control DNA can indicate mutations in the sample DNA. Moreover, the use of sequence-specific ribozymes (see, for example, U.S. Pat. No. 5,498,531) can be used to score for the presence of specific mutations by development or loss of a ribozyme cleavage site.

Genetic mutations in a KIF18A gene can be identified by hybridizing sample and control nucleic acids (e.g., DNA or RNA) to two-dimensional arrays, such as chip based arrays. Such arrays include a plurality of addresses, each of which is positionally distinguishable from the other. A different probe is located at each address of the plurality. The arrays can have a high density of addresses. For example, the arrays can contain hundreds or thousands of oligonucleotides probes (Cronin et al., *Human Mutation*, 7:244-255, 1996; Kozal et al., *Nature Medicine*, 2:753-759, 1996). In one alternative, genetic mutations in KIF18A can be identified in two-dimensional arrays containing light-generated DNA probes as described in Cronin et al. (supra). According to this method, a first hybridization array of probes can be used to scan through long stretches of DNA in a test sample and control sample to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

Any of a variety of sequencing reactions known in the art can be used to directly sequence the KIF18A gene and detect mutations by comparing the sequence of the sample KIF18A with the corresponding wild-type (control) sequence. Automated sequencing procedures can be utilized when performing the diagnostic assays (Biotechniques 19:448, 1995), including sequencing by mass spectrometry.

Other methods for detecting mutations in the KIF18A gene include methods in which protection from cleavage agents is used to detect mismatched bases in RNA/RNA or RNA/DNA heteroduplexes (Myers et al., *Science,* 230:1242, 1985; Cotton et al., *Proc. Natl. Acad. Sci. USA,* 85:4397, 1988; and Saleeba et al., *Methods Enzymol.,* 217:286-295, 1992).

The mismatch cleavage reaction employs one or more polypeptides that can recognize mismatched base pairs in double-stranded DNA (so called "DNA mismatch repair" enzymes) in defined systems for detecting and mapping point mutations in KIF18A cDNAs obtained from samples of cells. For example, the mutY enzyme of *E. coli* cleaves A at G/A mismatches and the thymidine DNA glycosylase from HeLa cells cleaves T at G/T mismatches (Hsu et al., *Carcinogenesis,* 15:1657-1662, 1994; U.S. Pat. No. 5,459,039).

In other embodiments, alterations in electrophoretic mobility will be used to identify mutations in KIF18A genes. For example, single strand conformation polymorphism (SSCP) can be used to detect differences in electrophoretic mobility between mutant and wildtype nucleic acids (Orita et al., *Proc. Natl. Acad. Sci USA,* 86:2766, 1989, see also Cotton, *Mutat. Res.* 285:125-144, 1993; and Hayashi, *Genet. Anal. Tech. Appl.* 2:73-79, 1992). Single-stranded DNA fragments of sample and control KIF18A nucleic acids can be denatured and allowed to renature. The secondary structure of single-stranded nucleic acids varies according to sequence, and the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In one embodiment, the subject method utilizes heteroduplex analysis to separate double-stranded heteroduplex molecules on the basis of changes in electrophoretic mobility (Keen et al., *Trends Genet.,* 7:5, 1991).

The movement of mutant or wild-type fragments in polyacrylamide gels containing a gradient of denaturant is assayed using denaturing gradient gel electrophoresis (DGGE) (Myers et al., *Nature,* 313:495, 1985). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner, *Biophys. Chem.,* 265:12753, 1987).

Examples of other techniques for detecting point mutations include, but are not limited to, selective oligonucleotide hybridization, selective amplification, or selective primer extension (Saiki et al., *Nature,* 324:163, 1986; Saiki et al., *Proc. Natl Acad. Sci USA,* 86:6230, 1989).

Alternatively, allele-specific amplification technology that depends on selective PCR amplification can be used to detect nucleotide polymorphisms. Oligonucleotides used as primers for specific amplification can carry the mutation of interest in the center of the molecule (so that amplification depends on differential hybridization) (Gibbs et al., *Nucleic Acids Res.,* 17:2437-2448, 1989) or at the extreme 3' end of one primer where, under appropriate conditions, mismatch can prevent, or reduce polymerase extension (Prossner, *Tibtech,* 11:238, 1993). In addition it may be desirable to introduce a novel restriction site in the region of the mutation to create cleavage-based detection (Gasparini et al., *Mol. Cell Probes,* 6:1, 1992). It is anticipated that in certain embodiments, amplification can also be performed using Taq ligase for amplification (Barany, *Proc. Natl. Acad. Sci. USA,* 88:189, 1991). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose subjects exhibiting symptoms or family history of a disease or illness involving a KIF18A gene, or to assess the effect of treatment with a pharmaceutical composition of the method on KIF18A activity. For example, a subject can come from a family with a history of a proliferative disorder, such as cancer (e.g., any of the types of cancers described herein) or psoriasis or atopic dermatits. A subject can alternatively, or in addition, come from a family with a history of autoimmune disease, such as rheumatoid arthritis or any of the other autoimmune disorders described herein. A patient who experiences any symptoms of a proliferative or autoimmune disorder can receive or perform the methods of any of the kits described herein.

Pharmaceutical Compositions

Therapeutic nucleic acids, polypeptides, antibodies, small non-organic molecules and small non-nucleic acid organic molecules that modulate the activity or expression of KIF18A (also referred to herein as "modulating agents" or "active compounds") can be incorporated into pharmaceutical compositions. Such compositions typically include the active compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous; oral (e.g., inhalation); transdermal (topical); transmucosal; and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage, and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent, such as aluminum monostearate or gelatin, which delays absorption.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the modulating agents are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the modulating agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of polypeptide (i.e., an effective dosage) ranges from about 0.001 to 30 mg/kg body weight, for example about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, or 5 to 6 mg/kg body weight. The polypeptide can be administered one time per week for between about 1 to 10 weeks, for example, between 2 to 8 weeks, between about 3 to 7 weeks, or for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a polypeptide or antibody can include a single treatment or a series of treatments.

For antibodies, the dosage can be about 0.1 to 100 mg, e.g., 10 to 60 mg/kg, or 20 to 40 mg/kg. If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). A method for lipidation of antibodies is described by Cruikshank et al. (*J. Acquired Immune Deficiency Syndromes and Human Retrovirology,* 14:193, 1997).

Compounds that modulate expression or activity of a KIF18A polypeptide or nucleic acid can be included in the pharmaceutical compositions described herein. A compound can, for example, be a small molecule. Such small molecules include, but are not limited to, polypeptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 µg/kg to about 500 mg/kg, about 100 µg/kg to about 5 mg/kg, or about 1 µg/kg to about 50 µg/kg). It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety can be a polypeptide possessing a desired biological activity. Such polypeptides can include, for example, a toxin such as abrin, ricin A, pseudomonas exotoxin, or diphtheria toxin; a polypeptide such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., *Proc. Natl. Acad. Sci. USA,* 91:3054-3057,1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

Described herein are methods, including prophylactic and therapeutic methods, of treating a subject having or at risk for developing (or susceptible to) a disorder associated with aberrant or unwanted KIF18A expression or activity. Aberrant or unwanted expression or activity can refer to overexpression or increased KIF18A activity, or a loss or decrease in KIF18A expression or activity. In one aspect, the invention provides methods for preventing in a subject, a disease or condition associated with increased KIF18A expression or activity, by administering to the subject a compound that inhibits KIF18A expression or at least one KIF18A activity. A subject having an increased KIF18A expression or activity may have, e.g., a proliferative disorder, such as psoriasis or a cancer. Also described herein are methods for preventing in a subject, a disease or condition associated with decreased KIF18A expression or activity, by administering to the subject a KIF18A nucleic acid or polypeptide, or a compound that stimulates or increases KIF18A expression or at least one KIF18A activity. Decreased KIF18A expression or activity may result in diseases or disorders resulting from inefficient cell replication, e.g., disorders characterized by inefficient wound healing or infertility.

Subjects having or at risk for a disease that is caused or contributed to by aberrant or unwanted KIF18A expression or activity can be identified by, for example, any or a combination of diagnostic or prognostic assays as described herein.

Administration of a prophylactic compound can occur prior to the manifestation of symptoms characteristic of a KIF18A aberrance, such that a disease or disorder is prevented or, alternatively, delayed in its progression. Depending on the desired effect of a KIF18A target compound, for example, a KIF18A agonist or KIF18A antagonist compound can be used for treating the subject. The appropriate compound can be determined based on screening assays described herein.

Some disorders can be caused, at least in part, by an abnormal level of gene product, or by the presence of a gene product exhibiting abnormal activity. As such, the reduction in the level and/or activity of such gene products can bring about the amelioration of disorder symptoms.

As discussed above, KIF18A disorders can be ameliorated by inhibiting the expression or activity of target gene products. For example, compounds, such as a compound identified using an assay described herein, that exhibit negative modulatory activities, can be used in accordance with the described treatment methods to prevent and/or ameliorate symptoms of a KIF18A disorder. Such molecules can include, but are not limited to polypeptides, phosphopeptides, small organic or inorganic molecules, or antibodies (including, for example, polyclonal, monoclonal, humanized, anti-idiotypic, chimeric or single chain antibodies, and Fab, F(ab')2 and Fab expression library fragments, scFV molecules, and epitope-binding fragments thereof).

Antisense, siRNA, and ribozyme molecules that inhibit expression of the target gene can also be used to reduce the level of KIF18A gene expression, thus effectively reducing the level of gene activity. Still further, triple helix molecules can be utilized in reducing the level of KIF18A gene activity. These molecules are described in detail above.

It is possible that the use of antisense, siRNA, ribozyme, and/or triple helix molecules to reduce or inhibit mutant gene expression can also reduce or inhibit the transcription (triple helix or siRNA) and/or translation (antisense, ribozyme, or siRNA) of mRNA produced by a normal KIF18A allele, such that the concentration of normal target gene product present can be lower than is necessary for a normal phenotype. In such cases, nucleic acid molecules that encode and express KIF18A polypeptides exhibiting normal polypeptide activity can be introduced into cells via a gene therapy method.

Another method by which nucleic acid molecules can be utilized in treating or preventing a disease characterized by KIF18A expression includes the use of aptamer molecules specific for a KIF18A polypeptide. Aptamers are nucleic acid molecules having a tertiary structure that permits them to specifically bind to polypeptide ligands (see, e.g., Osborne et al., *Curr Opin. Chem. Biol.*, 1:5-9, 1997; and Patel, *Curr. Opin. Chem. Biol.*, 1:32-46, 1997). Since nucleic acid molecules can, in many cases, be more conveniently introduced into target cells than therapeutic polypeptide molecules, aptamers offer a method by which KIF18A polypeptide activity can be specifically decreased without the introduction of drugs or other molecules which may have pluripotent effects.

Antibodies can be generated that are both specific for a KIF18A polypeptide and that reduce KIF18A polypeptide activity. Such antibodies may, therefore, be administered in instances whereby negative modulatory techniques are appropriate for the treatment of a KIF18A disorder. For a description of antibodies, see the "Antibodies" section above.

In circumstances wherein injection of an animal or a human subject with a KIF18A polypeptide or epitope for stimulating antibody production is harmful to the subject, or is otherwise undesirable, it is possible to generate an immune response against KIF18A through the use of anti-idiotypic antibodies (see, for example, Herlyn, *Ann. Med.*, 31:66-78, 1999; and Bhattacharya-Chatterjee and Foon, *Cancer Treat. Res.*, 94:51-68, 1998). If an anti-idiotypic antibody is introduced into a mammal or human subject, it should stimulate the production of anti-idiotypic antibodies, which should be specific to the KIF18A polypeptide. Vaccines directed to a disease characterized by KIF18A expression can also be generated in this fashion.

In instances where the KIF18A target antigen is intracellular and whole antibodies are used, internalizing the antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, polypeptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., *Proc. Natl. Acad. Sci. USA*, 90:7889-7893, 1993).

Compounds identified as inhibitors of KIF18A expression, synthesis, and/or activity can be administered to a subject at therapeutically effective doses to prevent, treat, or ameliorate KIF18A-mediated disorders. A therapeutically effective dose refers to that amount of the compound sufficient to result in amelioration of symptoms of a disorder. For example, a proliferative disorder, such as a cancer, is a KIF18A-mediated disorder that can be treated with a therapeutically effective dose of an identified compound. It is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated. A pharmaceutical composition of the invention is formulated to be compatible with its intended route of administration. Examples of routes of administration include oral or parenteral (e.g., intravenous, intradermal, subcutaneous, inhalation, transdermal (topical), transmucosal, and rectal administration (supra)). The specific KIF18A disease or disorder to be treated can direct an appropriate route of administration. For example, a subject having a wound healing disorder due to insufficient KIF18A expression or activity, can be administered a topical solution, such as a cream or lotion, containing KIF18A or a modulating agent that increases KIF18A expression or activity.

Toxicity and therapeutic efficacy of such compounds can be determined by standard pharmaceutical procedures in cell cultures or experimental animals, such as for determining the LD50 and the ED50 as described above in the Pharmaceutical Compositions section.

Another aspect of the invention pertains to methods of modulating KIF18A expression or activity for therapeutic purposes. Accordingly, in one embodiment, the modulatory method of the invention involves contacting a cell with KIF18A or compound that modulates one or more of the activities of KIF18A polypeptide activity associated with the cell. A compound that modulates KIF18A protein activity can be a compound as described herein, such as a nucleic acid or a polypeptide, a naturally-occurring target molecule of a KIF18A polypeptide (e.g., a microtubule), a KIF18A antibody, a KIF18A agonist or antagonist, a peptidomimetic of a KIF18A agonist or antagonist, or other small molecule (e.g., a small inorganic molecule).

A compound described herein may stimulate one or more KIF18A activities. Examples of such stimulatory agents include active KIF18A polypeptide and a nucleic acid molecule encoding KIF18A. Alternatively, the compound may inhibit one or more KIF18A activities. Examples of such inhibitory compounds include antisense KIF18A nucleic acid molecules, anti-KIF18A antibodies, and KIF18A inhibitors. These modulatory methods can be performed in vitro (e.g., by culturing the cell with the compound) or, alternatively, in vivo (e.g., by administering the compound to a subject). As such, methods are described for the treatment of an individual afflicted with a disease or disorder characterized by aberrant or unwanted expression or activity of a KIF18A polypeptide or nucleic acid molecule. One such method involves administering a compound (e.g., a compound identified by a method, such as a screening assay, described herein), or combination of compounds that can modulate (e.g., upregulate or downregulate) KIF18A expression or activity. In addition, or in an alternative, a KIF18A polypeptide or nucleic acid molecule can be administered as a therapy to compensate for reduced, aberrant, or unwanted KIF18A expression or activity.

Stimulation of KIF18A activity can be desirable in situations in which KIF18A is abnormally downregulated and/or in which increased KIF18A activity is likely to have a beneficial effect. Likewise, inhibition of KIF18A activity can be desirable in situations in which KIF18A is abnormally upregulated and/or in which decreased KIF18A activity is likely to have a beneficial effect.

Uses

Methods of identifying a compound that modulates the expression or activity of a KIF18A gene or polypeptide are described herein. For example, one method includes contacting the compound with a KIF18A polypeptide and evaluating the ability of the compound to interact with (e.g., to bind or form a complex with) the subject KIF18A polypeptide. Such methods can be performed in vitro, such as in a cell free system, or in vivo, such as in a two-hybrid interaction assay. Such methods can be also be used to identify naturally occurring molecules that interact with a subject KIF18A polypeptide. They can also be used to find natural or synthetic inhibitors of a subject KIF18A polypeptide. Screening methods are discussed in more detail above.

Antibodies described herein can be used in one or more of the following methods without limitation: a) screening assays; b) predictive medicine (e.g., diagnostic assays and monitoring clinical trials); and c) methods of treatment (e.g., therapeutic and prophylactic). More specifically, the anti-KIF18A antibodies of the invention can be used to detect and isolate related kinesin-like polypeptides, regulate the bioavailability of KIF18A and related polypeptides, and modulate the activity of KIF18A and related polypeptides.

The therapeutic agents described herein can target a cell (or cells) of interest, such as a tumor cell, in the case of a cancer, or a cell of a joint in the case of rheumatoid arthritis. For example, a therapeutic nucleic acid molecule, such as an siRNA or antisense nucleic acid, can be conjugated to a ligand that binds a receptor presented on the surface of a target cell, such as a cancer cell. Alternatively, a therapeutic nucleic acid molecule can be conjugated to an antibody that recognizes a ligand present on a target cell. For example, an antibody that binds c-erbB-2, CO17-1A, MUC-1, or LewisY antigen can be conjugated to a therapeutic agent to treat breast cancer cells (Braun et al., Int. J. Cancer 84: 1-5, 1999). In yet another alternative, a therapeutic polypeptide can be a fusion polypeptide, wherein the therapeutic amino acid sequence is fused to an amino acid sequence that can bind a receptor or ligand on the surface of a target cell.

The new methods and compounds (including antibodies) described herein can be used as an insecticide, such as by targeting KLP67A. For example, an antibody or compound that inhibits KLP67A gene expression or polypeptide activity can be ingested by an insect, which can result in death or sterility of the insect. In another alternative, an agent that targets KLP67A can be distrubuted by a viral vector. For example, a virus carrying a nucleic acid encoding an agent (such as a dsRNA or antisense RNA) that targets KLP67A expression or activity can be used to infect insects.

The invention is further illustrated by the following examples, which should not be construed as further limiting.

EXAMPLES

Example 1

Materials and Methods for Analysis of the Role of Drosophila KLP67A in Mitosis

KLP67A is the Drosophila ortholog of KIF18A (Miki et al., Proc. Natl. Acad. Sci. USA, 98:7004-7011, 2001). Thus an analysis of the role of KLP67A in the genetically tractable model organism Drosophila melanogaster, can provide insight to the role of KIF18A in vertebrate cells, such as mammalian cells (e.g., human cells).

Vectorette Screen for P Insertions at KLP67A

The procedure of Eggert et al. (Genetics 149:1427-1434, 1998) was followed with the following modifications to recover P element insertions in KLP67A. As a source of P, the strain 1(3)036912 was used as a source of P (Deak et al., Genetics, 147:1697-1722, 1997), since we had molecularly mapped the P element in this strain to 10 kb from the 3' end of the KLP67A gene by plasmid rescue. Animals of the genotype w$^-$; 1(3)036912 were crossed to a strain containing the immobilized source of P transposase, P[Δ2-3]. Resulting male progeny with the genotype w$^-$; 1(3)036912/P[Δ2-3] were then crossed to w$^-$;TM6B females. To screen for insertions in KLP67A, DNA was prepared from pools of 35-50 w$^+$ progeny and used as a template for vectorette mediated inverse PCR as described (Eggert et al., Genetics 149:1427-1434, 1998). To determine the precise insertion site of a potential P element in KLP67A, PCR reactions were performed with genomic DNA using a P element-specific primer (5'-CCACCTTATGTTATTTCATCATG-3' (SEQ ID NO:15)) and a KLP67A-specific primer (5'-CCTTGAATCGCACTC-CAATGC-3' (SEQ ID NO:16)). The resulting 900 bp DNA fragment was purified and sequenced using these same primers.

Screen for Local P Transpositions

Animals of the genotype w$^+$; EP(3)3516/TM6B were crossed to a strain containing the immobilized source of P transposase, P[Δ2-3]. Resulting male progeny with the genotype w$^-$; EP(3)3516/[Δ2-3] were then crossed as single pair matings to w$^-$;Df(3L)29A6/TM6B female. To screen for local hops, DNA was prepared from pools of progeny and 200 mutagenized lines were screened by PCR with primers specific to P and internal to KLP67A as described above. A size change in the PCR product or its absence indicated a putative deletion.

Construction of Rescue Construct Pwum$^2$[myc:KLP67A]

A KLP67A cDNA was cloned into the BamH I/EcoR I sites of the P element transformation vector Pwum$^2$ (Heck et al., J.

Cell Biol., 123:665-679, 1993) that allowed KLP67A to be expressed as a fusion protein with a myc epitope at the amino terminus. Germ line transformants with chromosome II insertions of Pwum$^2$[myc:KLP67A] were recovered and kept as homozygotes. Pwum$^2$[myc:KLP67A] was also put into the background of Df(3L)29A6/TM6B (A.T.C. Carpenter unpublished data). For rescue crosses animals of the genotype w$^-$;Pwum$^2$[myc:KLP67A]; Df(3L)29A6/TM6B were crossed to KLP67A$^{322b24}$/TM6B and the resulting progeny which were w$^-$; Pwum$^2$[myc:KLP67A]; Df(3L)29A6/ KLP67A$^{322b24}$ were tested for male fertility.

RT-PCR Analysis of Insertion Lines mRNA was prepared from both mutant and wildtype testes and cDNA was then synthesized using a Qiagen RT-PCR kit (Valencia, Calif.). To detect transcription from KLP67A, a primer specific to the middle of P[lacW] (5'-CACCCAAG-GCTCTGCTCCCACAAT-3') (SEQ ID NO:5) together with a KLP67A reverse primer specific to the coding sequence (5'-CCCACATCGAATTTGCGC-3') (SEQ ID NO:6) were used to amplify the KLP67A cDNA. The resulting PCR product was then sequenced to verify that the transcript did indeed contain sequences encoded by the P[lac] element.

Immunofluorescence Analysis of Male Sterile Mutations

Testes were dissected and fixed according to Cenci et al. (J. Cell Sci., 107:3521-3534, 1994) for α-tubulin and either centrosomin or myosin II immunostaining, and to Gunsalus et al. (J. Cell Biol., 131:1234-1259, 1995) for α-tubulin immunostaining followed by actin staining with phalloidin. Slides were rinsed several times in phosphate buffered saline (PBS) and then incubated overnight at 4° C. with anti-centrosomin (Li and Kaufman, Cell 85:585-596, 1996) or anti-myosin II (provided by Chris Field, Harvard University; Foe et al., Development, 127:1767-1787, 2000) rabbit primary antibodies diluted in PBS. Primary antibodies were detected by a 2 hour incubation at room temperature with Cy3 conjugated anti-rabbit IgG (Harlan Sera-Lab; Leicestershire, England) diluted 1:30 in PBS. Slides were then incubated for 1 hour at room temperature with a monoclonal anti α-tubulin antibody (Amersham; Piscataway, N.J.) diluted 1:50 in PBS and then with FITC-conjugated sheep-anti-mouse IgG diluted 1:20 (1 hour at room temperature; Jackson ImmunoResearch Laboratories; West Grove, Pa.). For actin plus tubulin staining, testes were first immunostained for α-tubulin as described and then incubated with rhodamine-phalloidin (Molecular Probes; Eugene, Oreg.) as described in Gunsalus et al. (J. Cell Biol., 131:1243-1259, 1995). All preparations were mounted with Vectashield H-1200 with DAPI (Vector Laboratories; Burlingame, Calif.) and examined with an AxioPlan (ZEISS) microscope equipped with a 50 W mercury lamp for epifluorescence and with a cooled charge-coupled device (CCD; Biomedical Photometrics Inc.; Waterloo, Ontario, Canada). Grayscale digital images were collected using IP Lab Spectrum software and then converted to Photoshop 5.0 format, pseudocolored and merged.

Live Confocal Imaging

For time-lapse confocal microscopy, early embryos (0-2 hours) were manually dechorionated, transferred to adhesive-coated coverslips, and briefly dehydrated to accommodate the addition of injected material. The dehydrated embryos were then covered with halocarbon oil and transferred to the stage of the confocal microscope. A fluorescent conjugate of tubulin (tetramethylrhodamine-tubulin; Cytoskeleton Inc.; Denver, Colo.) was then microinjected into the embryos at a concentration of 5 μg/mL. The behavior of the labeled tubulin was visualized directly using a Leica TCS-SP laser-scanning confocal microscope as described in Theurkauf and Heck (Methods Cell Biol., 61:317-346, 1999).

Cell Culture and Transfection of KLP67A dsRNA

Drosophila cultured cells (DL2) were grown at room temperature in Schneider's Drosophila medium supplemented with 10% fetal bovine serum and 1× penicillin streptomycin solution. DL2 cells, derived from the Drosophila Schneider cell line, SL2, were provided by Norbert Perrimon, Harvard Medical School. For transfection, cells were resuspended and cultured at 2×10$^5$ cells/mL in a 24 well dish with and without coverslips for 24 hours before transfection. Cells were transfected using standard calcium phosphate methods with 5 μg KLP67A dsRNA (FIG. 21; SEQ ID NO:14) per well in 1 mL medium. After 16-18 hours of transfection, cells were washed with fresh medium and cultured for another 24 hours before staining for immunofluorescence or assaying by RT-PCR.

To prepare for immunofluorescence staining, cells were fixed in methanol and immunostained for α-tubulin (Sigma; St. Louis, Mo.), centrosomin (Heuer et al., Development, 121:3861-76, 1995; Li and Kaufman, Cell, 85:585-96, 1996; provided by T. Kaufman, Indiana University; Bloomington, Ind.) and DAPI (Sigma; St. Louis, Mo.).

For synthesizing dsRNA, a 500 bp fragment of KLP67A was PCR amplified using gene-specific primers, 5'-T7-AG-TACGGCCGTATAATGTCCGTG-3' (SEQ ID NO:7) and 5'-T7-CCACTGACCACCACGCCATTG-3' (SEQ ID NO:8) to allow in vitro transcription from both strands of the 500 bp KLP67A PCR fragment. For synthesizing KLP61F dsRNA (FIG. 20; SEQ ID NO:13), gene-specific primers, 5'-T7-GACGGGCACAGGGAAGACCCAC-3' (SEQ ID NO:9) and 5'-T7-TCCCTTTTCATTCCCAGCCTTGG-3' (SEQ ID NO:10) were used. An Ambion MEGAscript™ T7 kit (cat#1334; Austin, Tex.) was used for the in vitro transcription reaction. The RNA was precipitated with lithium chloride and dissolved in water. It was annealed by heating at 1% agarose gel and quantified by UV spectrophotometry. For RT-PCR, the RNA was isolated from cells using a Qiagen RNeasy® Mini Kit (Qiagen Inc.; Valencia, Calif.) and amplified employing Qiagen One-Step RT-PCR Kit with KLP67A gene-specific primers (5'-CGAAAACCAAACAAGAGC-3' (SEQ ID NO:11) and 5'-CCCACATCGAATTTGCGC-3' (SEQ ID NO:12)).

Example 2

Isolation of Mutations in the KLP67A Gene

To examine the role of the kinesin-like protein KLP67A in cell proliferation, a vectorette-mediated PCR screen was used to isolate mutations in the Drosophila KLP67A gene (Eggert et al., Genetics, 149:1427-1434, 1998). To conduct this screen, pre-existing P element insertions in the 67A region were molecularly mapped to the cloned KLP67A interval. Plasmid rescue of several of the previously identified P element lines at 67A (Deak et al., Genetics, 147:1697-1722, 1997) revealed that two of these insertions were close to the 3' end of the KLP67A gene. Strain l(3)036912 contains a P element within 6 kb of the gene, and strain l(3)049508 contains an element within 11 kb of the 3' end of the gene. In two separate vectorette screens, these elements were mobilized and insertions in KLP67A were assayed by PCR of genomic DNA that had been restriction digested and ligated to a vectorette fragment (Eggert et al., Genetics, 149:1427-1434, 1998). For each screen, pooled samples of genomic DNA, prepared from 1000 mutagenized lines of flies, were used for the PCR reactions and then the products were probed with a KLP67A cDNA (GenBank Accession No. NM_079268; SEQ ID NO:4; FIG. 19).

Several pools of DNA contained a P element insertion at the same site indicating that KLP67A contains a "hot spot" for P element integration. DNA sequence analysis of the PCR fragment resulting from positive line, P[lac w] 15D, revealed that the hotspot is 130 bp upstream from the transcription start of KLP67A. Upon completion of this screen, a P element insertion, EP(3)3516, was identified in this same location from the Rorth collection (Rorth, *Genetics*, 93:12418-12422, 1996) during the *Drosophila* genome sequencing project (Spradling et al., *Proc. Natl. Acad. Sci. USA*, 92:10824-10830, 1995). These insertions were found to be homozygous viable. They also had no phenotype when made heterozygous over the deficiency Df(3L)29A6 that lacks the KLP67A sequence.

A second type of PCR screen for "local hops" (Tower et al., *Genetics*, 133:347-359, 1993) as well as P transposition associated aberrations was conducted using the EP(3)3516 element (Rorth, *Proc. Natl. Acac. Sci.*, 93: 12418, 1996; the sequence of the EP element was compiled at the internet-based database, Flybase (Gelbart, W. M., 1994. Personal communication), and has the designation Fbmc0001297). The element was mobilized in males and the F2 generation was screened for eye color changes including white eyes. Potential mutations were assayed by PCR using a P element-specific primer as well as a KLP67A gene-specific primer. PCR reactions were examined for either an altered size fragment or an absence of product. Twenty potential mutations were isolated from 200 lines screened. DNA sequence analysis of several of these lines revealed that they contained small deletions of 35 bp or fewer within the promoter region of KLP67A. One of these lines, designated KLP67A$^{322b24}$, was then used for further characterization. It was determined by RT-PCR analysis that KLP67A transcription begins within the rosy (ry) gene of the P element, which was inserted 130 bp upstream of the transcription start site for KLP67A (155 bp upstream of the start codon for the KLP67A ORF). The insertion corresponds to bp position 9,317,954 of GenBank Accession Number NT_037436.

Example 3

The Meiotic Phenotype of KLP67A Mutants

KLP67A$^{322b24}$/Df(3L)29A6 flies were viable and did not exhibit a visible phenotype. However, males of this genotype were either sterile or semi-sterile. Testes from KLP67A$^{322b24}$/Df(3L)29A6 males were dissected, squashed, and examined cytologically for the presence of meiotic defects. As shown in FIGS. 1-11, a number of microtubule-related defects were observed throughout all stages of the first meiotic division. First, in 89% (n=74) of late prophase images (stage M1 according to Cenci et al., *J. Cell Sci.*, 107:3521-3534, 1994), the asters were not properly positioned at the opposite sides of the nucleus as in wildtype (see FIG. 1) but ectopically localized in the cytoplasm and close to each other, as demonstrated in FIG. 2; occasionally, centrosomes and their associated asters appeared to detach from the poles, giving rise to asters that freely float in the cytoplasm (see FIG. 3). In other cases, evidence failed cytokinesis in a gonial division could be found in tetraploid spermatocytes. These spermatocytes also demonstrated ectopically positioned asters (see FIG. 4).

Figure 5:
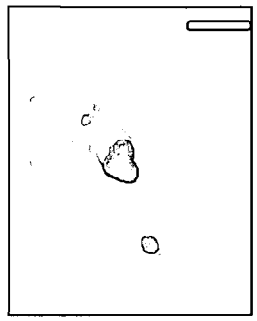
FIG. 5 is a photomicrograph of a spermatocyte isolated from the testes of wildtype *Drosophila* and stained for α-tubulin, centrosomin, and DNA. The spermatocyte is in the metaphase I stage of meiosis.
Figure 6:
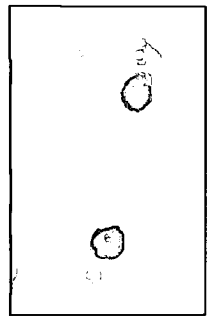
FIG. 6 is a photomicrograph of a spermatocyte isolated from the testes of wildtype *Drosophila* and stained for α-tubulin, centrosomin, and DNA. The spermatocyte is in the anaphase I stage of meiosis.
Figure 7:
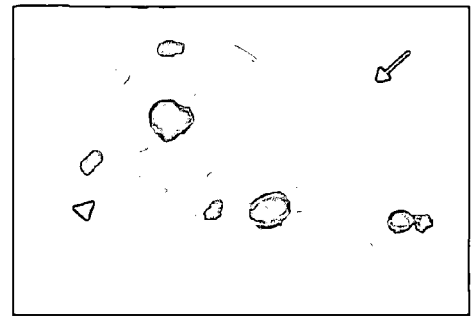
FIG. 7 is a photomicrograph of two spermatocytes isolated from the testes of the *Drosophila* Df(3L)29A6/KLP67A$^{322b24}$ mutant and stained for α-tubulin, centrosomin, and DNA. The metaphase I spermatocyte (left; arrowhead) has a bipolar spindle. The anaphase I spermatocyte (right; arrow) demonstrated abnormal chromosome segregation. In both cells, the microtubules appear longer than in wildtype spermatocytes (see FIGS. 5, 6, 8, 10).
Figure 8:
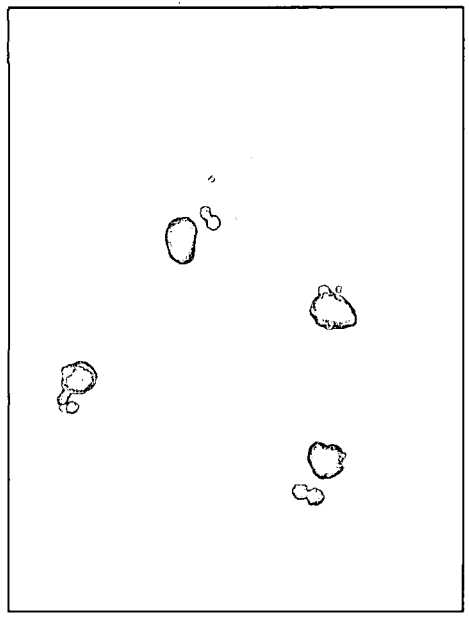
FIG. 8 is a photomicrograph of two spermatocytes isolated from the testes of wildtype *Drosophila* and stained for α-tubulin, centrosomin, and DNA. The spermatocytes are in the telophase I stage of meiosis.
Figure 9:
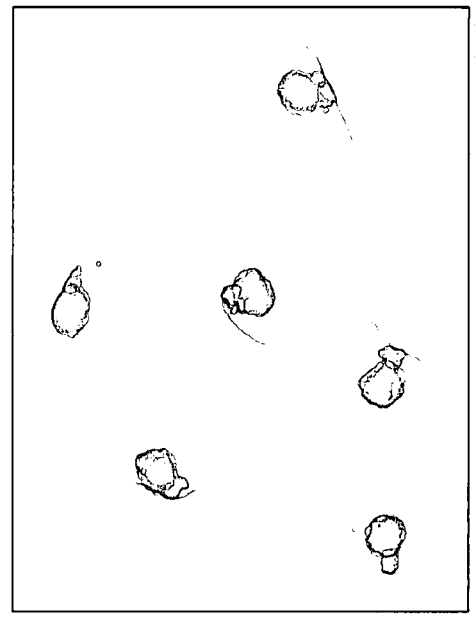
FIG. 9 is a photomicrograph of three spermatocytes isolated from the testes of the *Drosophila* Df(3L)29A6/KLP67A$^{322b24}$ mutant and stained for α-tubulin, centrosomin, and DNA. These telophase I spermatocytes demonstrate abnormally long astral microtubules and abnormal central spindles.
Figure 10:
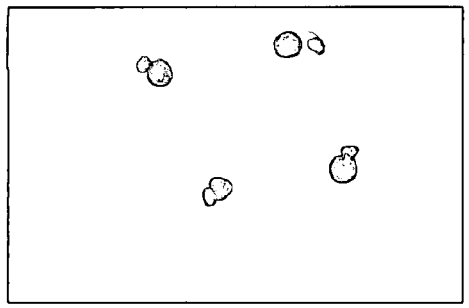
FIG. 10 is a photomicrograph of two spermatocytes isolated from the testes of wildtype *Drosophila* and stained for α-tubulin, centrosomin, and DNA. The spermatocytes are in the telophase II stage of meiosis.
Figure 11:
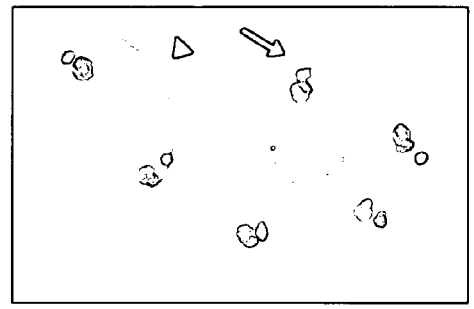
FIG. 11 is a photomicrograph of telophase II spermatocytes isolated from the testes of the *Drosophila* Df(3L)29A6/KLP67A$^{322b24}$ mutant and stained for α-tubulin, centrosomin, and DNA. The arrowhead points to a morphologically abnormal telophase figure in which interpolar microtubules overlap in the middle of the cell but do not form a typical dense central spindle. The arrow points to two telophases within the same cytoplasm showing long astral microtubules. Generally, the astral microtubules emanating from different spindles overlap in an abnormal fashion.

Despite the defect in aster localization and separation, most KLP67A primary spermatocytes (96%; n=52) appeared to progressively assemble a bipolar spindle, which could mediate the formation of a metaphase plate (FIG. 7, cell indicated by arrowhead) and to proceed through anaphase (FIG. 7, arrow). FIG. 5 shows a normal spermatocyte isolated from the testes of wildtype *Drosophila* in the metaphase I stage of meiosis. The spermtocyte is stained for α-tubulin, centrosomin, and DNA. The whiter spots represent the centrosomes. FIG. 6 shows a normal spermatocyte in the anaphase I stage of meiosis. Mutant metaphase and anaphase spindles both displayed astral MTs that appeared to be longer than their wildtype counterparts (see FIG. 7). In addition, in 12% of anaphase images (n=25) the two daughter nuclei were of different sizes, suggesting aberrant chromosome segregation (FIG. 7, arrow). Telophase I spindles of KLP67A spermatocytes were even more irregular. FIG. 8 is a photomicrograph of wildtype spermatocytes in telophase I, and FIG. 9 is a photomicrograph of KLP67A mutant spermatocytes in telophase I. In 60% (n=60) of telophase images, astral MTs were longer in mutant than in wildtype cells, and the central spindle was either absent or much less dense than that seen in normal cells (compare FIGS. 8 and 9). An examination of secondary spermatocytes undergoing the second meiotic division revealed that only 18% of late prophase images (n=60) exhibited ectopic aster localization. However, cells in subsequent stages of meiosis II exhibited the same defects observed in primary spermatocytes undergoing meiosis I. Interestingly, 47% of ana-telophase II images (n=132) displayed two spindles within the same cytoplasm (see FIG. 11), suggesting a failure of cytokinesis during the first meiotic division. In these "double" secondary spermatocytes, astral MTs were also long, so that MTs from asters of different spindles often overlapped, resulting in a highly disorganized spindle architecture (FIG. 11). Compare the mutant cells of FIG. 11 to the wildtype spermatocytes in FIG. 10, also in telophase II of meiosis.

To characterize the cytokinetic phenotype of KLP67A mutants, spermatocytes were stained for both myosin II and F actin, two well-known components of the contractile ring. By these studies, wildtype spermatocytes exhibited a robust central spindle and a clear acto-myosin ring. Mutant telophases that had normal central spindles also exhibited a regular contractile ring. However, mutant telophases with a poorly organized central spindle displayed a diffuse actin and myosin staining at the cleavage furrow rather than the typical tight band seen in wildtype cells. These results indicated that KLP67A telophases having a defective central spindle are unable to assemble a contractile ring and to undergo cytokinesis.

Spermatid morphology of KLP67A mutant spermatocytes was observed to determine the effect of the mutant-induced spindle defects. In wildtype spermatocytes, both chromosomes and mitochondria were equally partitioned between the two daughter cells at each meiotic division. After completion of meiosis, the mitochondria fused to form a conglomerate called the nebenkern. Thus, each wildtype spermatid contained a round nucleus associated with a single nebenkern of similar size. Defects in chromosome segregation resulted in differently sized nuclei (Gonzalez et al., *Genet. Res.*, 54:205-212, 1989), whereas failures in cytokinesis gave rise to spermatids having a large nebenkern associated with either two or four normal-sized nuclei (Fuller, *Spermatogenesis*. In: *The Development of Drosophila melanozaster*, Cold Spring Harbor Laboratory Press, Plainview, N.Y. Vol. I. M. Bate and A. M. Arias, eds., pp. 71-147, 1993). An examination of KLP67A mutant spermatids revealed that 41% of these cells (n=254) had large nebenkern associated with two or four nuclei. Twenty-four percent of the nuclei also displayed irregular sizes. Taken together, these observations suggested that KLP67A spermatocytes are defective in both chromosome segregation and cytokinesis.

Finally, it should be noted that a few spermatocytes were observed to be polyploid, having four rather than two centrosomes. This finding suggested that KLP67A is also required for cytokinesis during the gonial mitoses that precede meiotic division. Both the sterility and the meiotic phenotypes are completely rescued by the Pwum$^2$ [myc: KLP67A] transgene (see Example 1).

Example 4

KLP67A Maternal Effect on Embryonic Divisions

Females of the genotype KLP67A$^{322b24}$/Df(3L)29A6 exhibited reduced fertility compared to the parent strains KLP67A$^{322b24}$/TM6B and Df(3L)29A6/TM6B. Forty percent of the eggs laid by KLP67A$^{322b24}$/Df(3L)29A6 females hatched to first instar larvae compared to 96% of the eggs laid by a wildtype strain. To determine whether this maternal effect was due to a defect in early blastoderm mitoses, eggs from KLP67A$^{322b24}$/Df(3L)29A6 mothers crossed to wildtype males were collected and used for real time analysis of mitosis in living embryos. Rhodamine labeled tubulin was injected into living embryos and mitosis was allowed to proceed in real time. Time-lapse analysis of MTs showed that both spindle formation and architecture is abnormal through all stages of mitosis.

Figure 12:
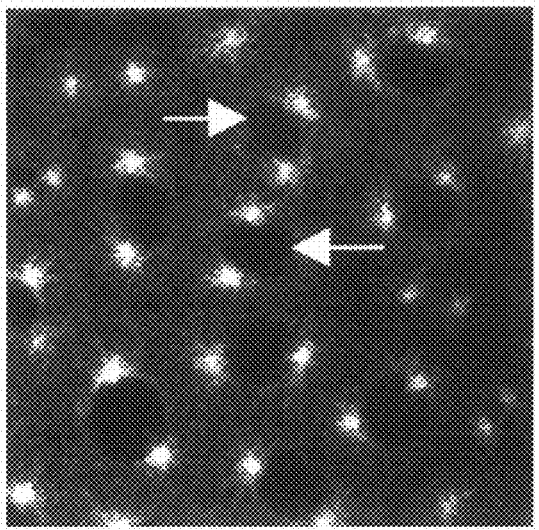
FIG. 12 is a photomicrograph representing the real time analysis of mitosis in blastoderm embryos of *Drosophila* Df(3L)29A6/KLP67A$^{322b24}$ mutants. Arrows draw attention to the correlation between incomplete centrosome separation and curved banana-shaped spindles (see FIG. 13).
Figure 13:
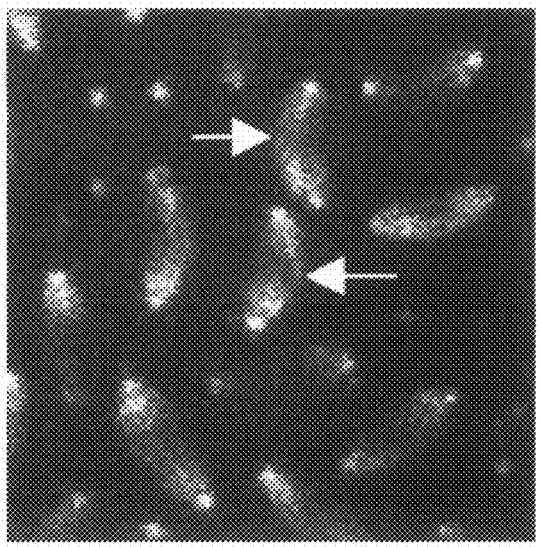
FIG. 13 is a photomicrograph representing the real time analysis of mitosis in blastoderm embryos of *Drosophila* Df(3L)29A6/KLP67A$^{322b24}$ mutants. Arrows draw attention to the correlation between curved banana-shaped spindles and incomplete centrosome separation (see FIG. 12).
Figure 14:
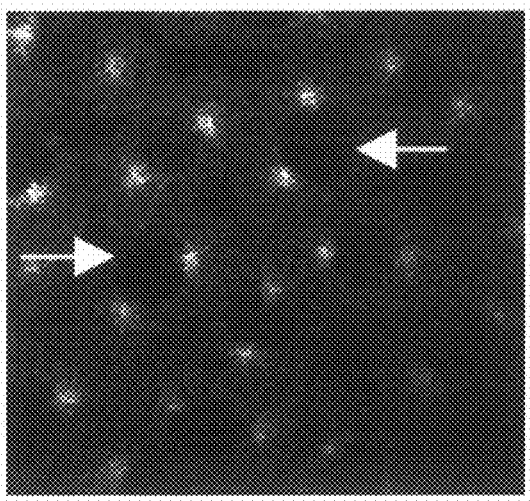
FIG. 14 is a photomicrograph representing the real time analysis of mitosis in blastoderm embryos of wildtype *Drosophila*. Arrows draw attention to the correlation between incomplete centrosome separation and curved banana-shaped spindles (see FIG. 15). The frequency of incomplete separation in wildtype embryos is less than that observed in Df(3L)29A6/KLP67A$^{322b24}$ embryos.
Figure 15:
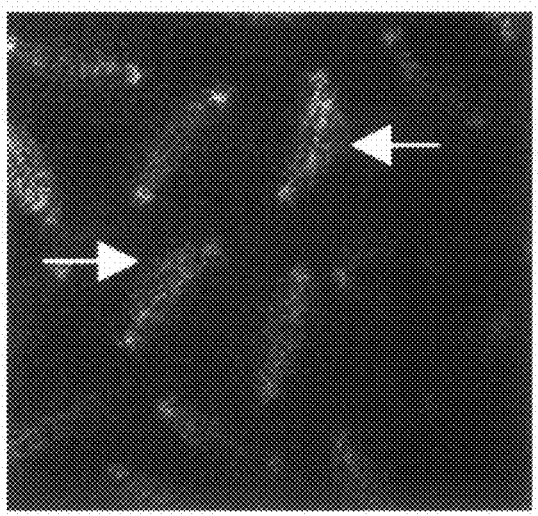
FIG. 15 is a photomicrograph representing a real time analysis of mitosis in blastoderm embryos of wildtype *Drosophila*. Arrows draw attention to the correlation between curved banana-shaped spindles and incomplete centrosome separation (see FIG. 14). The frequency of incomplete separation in wildtype embryos is less than that observed in Df(3L)29A6/KLP67A$^{322b24}$ embryos.

FIGS. 12-15 are photomicrographs representing the real time analysis of mitosis in the blastoderm of wildtype (FIGS. 14 and 15) and KLP67A$^{322b24}$/Df(3L)29A6 mutant (FIGS. 12 and 13) *Drosophila* embryos. Arrows draw attention to the correlation between incomplete centrosome separation (see FIGS. 12 and 14) and curved banana-shaped spindles (see FIGS. 13 and 15). During prophase, the majority of the centrosomes in the KLP67A$^{322b24}$/Df(3L)29A6 mutant embryos did not complete their migration to the opposite sides of the nucleus (FIG. 12, arrows). The average angle between prophase centrosomes (n=60) was observed to be 145.2° in mutants and 164.2° in wildtype embryos (n=54). This difference is statistically significant according to the student's T test (P=0.0002). These incompletely separated centrosomes then gave rise to curved banana-shaped spindles (FIG. 13). This centrosome migration defect was correlated with the misshapen spindle phenotype at metaphase in both wildtype and mutant embryos. However, in mutant embryos the malformation not only occurred more frequently, but it was also exacerbated. The time-lapse video also revealed that the distortion of the normal shape of the spindle occurred at the moment when dynamic MTs appeared to be extending downward to reach the chromosomes. At this precise moment the spindle became distorted and banana-shaped to accommodate the extended MTs emanating from the spindle poles (infra). In addition, some prometaphase and metaphase centrosomes detached from the spindle poles, as occurs during meiosis in mutant males. The timing of centrosome separation was also affected by a reduction in KLP67A. The period of centrosome migration up until the point of nuclear envelope breakdown lasted for at least 3 minutes; 1 minute longer than in wildtype embryos.

A second important feature of the mutant metaphase spindles was their increased length compared to wildtype spindles. The average pole-to-pole distance within the metaphase spindles (n=60) in mutant embryos was 15.6 μm (+/−1.5 SD) compared to 10.3 μm (+/−0.64 SD) in wildtype embryos (n=54). It is important to note that this increased spindle length was observed in all mutant spindles and was not a consequence of the defect in centrosome separation, as even those spindles with normal centrosome positioning were longer than their wildtype counterparts. In addition, in all types of spindles the increase in pole-to-pole length was clearly due to an increase in MT length. These results suggested that the activity of KLP67A is required for limiting the length of spindle MTs.

A third important feature of the KLP67A mutant phenotype was seen during telophase, when most spindles appeared to be either missing a normal central spindle or to have a greatly reduced number of midzone MTs. Central spindle formation normally occurs during anaphase when the overlapping set of anti-parallel interpolar MTs becomes bundled (Mastronarde et al., *J. Cell Biol.*, 123:1475-1489, 1993). Although areas of MT overlap existed, these MTs were not organized in the characteristic dense lateral arrays that characterize wildtype central spindles. This suggested that the abnormally long, and often curved or bent, astral MTs were not able to interact properly to give rise to the ordered parallel array of central spindle MTs. Since these early blastoderm mitoses did not require MTs to form the pseudo-cleavage furrow (Stevenson et al., *Nature Cell Biology*, 3:68-75, 2001), aberrant spindles were often able to proceed through telophase and two daughter spindles formed in the ensuing divisions. Chromosome behavior was also observed in eggs laid by KLP67A$^{322b24}$/Df(3L)29A6 females using real time analysis of eggs injected with OliGreen®. Despite the structural abnormalities observed in the spindles of these eggs, chromosome segregation appeared normal.

To analyze spindle dynamics in KLP67A mutant embryos, still images from time-lapse microscopy videos were used to measure the increase in spindle length during the interval between nuclear envelope breakdown (t=0 seconds) and the appearance of a central spindle (albeit drastically abnormal in the mutant embryo). This period lasted 2 minutes longer in mutant cells (360 seconds) than in wildtype cells (240 seconds). This difference was primarily due to an increase in the amount of time spent in metaphase and anaphase B. During metaphase, the mutant spindles continued to increase in length whereas their wildtype counterparts reached a plateau. In mutant embryos, however, the pause at metaphase (before the final spike in pole separation at anaphase B) was delayed and occurred later than in wildtype. Although wildtype and mutant spindles did not exhibit noticeable differences in the speed of chromosome movement during anaphase A, the mutant spindles took significantly longer to go through anaphase B (90 seconds in the mutants versus 30 seconds in the wildtype). This slowing of anaphase B may be related to the unusual S shaped conformation assumed by mutant spindles during pole separation.

An antibody specific for a KLP67A polypeptide (Pereira et al., *J. Cell Biol.*, 136:1081-1090, 1997) was used to assess the effect of the 322b24 mutation on KLP67A protein expression. Antibody staining of eggs derived from mutant mothers, as well as Western blot analysis, demonstrated that the KLP67A$^{322b24}$ allele only mildly affected protein expression levels; the intensity of antibody staining was almost equal to wildtype. Quantitation of Western blot experiments indicated the expression from the KLP67A$^{322b24}$ allele was about 11% less than expression from the wildtype allele. Together, these results indicate that MT polymerization and, as a result, spindle assembly is extremely sensitive to a slight decrease in the expression level of KLP67A during both male meiosis and embryonic mitoses.

These data demonstrate that it is not necessary to fully suppress expression or activity of KLP67A or a related gene, e.g., KIF18A, to elicit an effect on cellular proliferation. Thus, compounds that partially inhibit expression or activity of a KLP67A nucleic acid or polypeptide (or an orthologous nucleic acid or polypeptide, e.g., KIF18A) can be useful for inhibiting cellular proliferation.

Example 5

RNA Interference of KLP67A

A genetic null allele of KLP67A would greatly facilitate the functional analysis of this gene. Since a null allele had yet to be successfully generated (strongly suggesting that KLP67A is an essential gene), RNA interference (RNAi) was used to create a KLP67A null phenocopy. These experiments were performed using the DL2 Drosophila cell line. The flat morphology of these cells allowed a clear view of individual MTs, thereby permitting a reliable evaluation of the effect of KLP67A on MT length. Cells were transfected with a 500 bp double-stranded (ds) RNA, designed to target KLP67A (see Example 1). Transfected and mock-transfected cells were incubated for two days before they were harvested and fixed for visualization by immunofluorescence. Mitotic images were observed by indirect immunofluorescence. The frequencies of cells in the different stages of mitosis in the treated vs. control cells is recorded in Table 1. It was evident from these data that RNAi caused a mitotic block at metaphase. This suggests that the KLP67A RNAi cells were unable to progress to anaphase and telophase due to the activation of the mitotic checkpoint that prevented cells with defective spindles to enter anaphase.

Similar results were observed in a Snyder (SL2) cell line transfected with dsRNA targeted to KLP67A.

15 µM. This concentration of nocodazole destabilized MTs and perturbed spindle assembly in control DL2 cells, but only slightly affected spindle architecture and had no effect on astral MT arrays in KLP67A depleted cells. This demonstrated that inhibition of KLP67A expression or activity (or expression or activity of an ortholog, e.g., KIF18A) can be used to stabilize spindle assembly.

The RNAi phenotype observed in cultured cells corresponded to a strong mutant allele. RT-PCR analysis indicated that the KLP67A dsRNA treatment results in a significant decrease in the KLP67A mRNA after two days of treatment. Moreover, the RNAi phenotype was not an indirect effect of the mispositioning of the mitochondria since the location of mitochondria relative to the spindle was identical in treated and untreated cells.

Example 6

Double RNA Interference of KLP61F and KLP67A

The increase in MT length observed in KLP67A mutant cells could indicate a requirement for KLP67A in the regulation of MT length. Alternatively, KLP67A could be required for maintaining normal spindle pole separation, and the increased pole-to-pole distance in KLP67A mutant cells could result in an increased MT polymerization. To discriminate between these possibilities, monopolar spindles were examined for abnormal MT elongation in the absence of KLP67A. To perform this analysis, DL2 cells were co-transfected with both KLP61F dsRNA (FIG. 20; SEQ ID NO:13) and KLP67A dsRNA (FIG. 21; SEQ ID NO:14). Previous genetic analyses (Heck et al., *J. Cell Biol.*, 123:665-679,

TABLE 1

RNAi of KLP67A results in a mitotic arrest

| Transfection Condition | Mitotic Index | # of mitotic images | Prophase % | Prometaphase % | Metaphase % | Anaphase % | Telophase % |
|---|---|---|---|---|---|---|---|
| Control | 3.4[a] | 85 | 17.6 | 12.9 | 52.9 | 8.2 | 8.2 |
| KLP67A (RNAi) | 13.1[b] | 252 | 3.6 | 23.8 | 69.84 | 1.5 | 1.1 |

DL2 Cells were transfected with KLP67A dsRNA (KLP67A, RNAi) (FIG. 21; SEQ ID NO: 14) or mock transfected (control). The mitotic index is percentage of cells in mitosis, recorded after 2 days.
[a]n = 2,430;
[b]n = 1,923.

Although the metaphase arrest of KLP67A RNAi cells precluded observation of the entire mitotic process, certain aspects of the phenotype of these cells resembled the KLP67A maternal effect observed in blastoderm embryos. The spindles of dsRNA-transfected cells were extremely elongated. The pole-to-pole distance in the control spindles were less than half of that observed in the (RNAi) spindles. These enlarged spindles also showed interpolar MTs that were abnormally long and curved. In addition, the overall shape of these spindles was often curved as was observed in the blastoderm mitotic divisions (see FIGS. 13 and 15), again indicating incomplete centrosome separation. The metaphase chromosome configuration was also abnormal and a tight metaphase plate configuration was rarely seen.

The observed aberrations were most likely due to an increase in MT stability. To test this, nocodazole was added to control cultures and cultures transfected with KLP67A dsRNA (FIG. 21; SEQ ID NO:14) to a final concentration of 1993) and antibody injection experiments (Sharp et al., *J. Cell Biol.*, 144:125-138, 1999b) had shown that KLP61F depletion prevents centrosome separation, resulting in monopolar spindles. Similarly, treatment of DL2 cells with KLP61F dsRNA frequently produced spindles with unseparated asters. These monopolar spindles were associated with highly condensed chromosomes that appeared to be in metaphase. Transfection of DL2 cells with dsRNA targeting both KLP61F and KLP67A effectively reduced the expression of both mRNAs and also resulted in monopolar spindles. However, these monopolar spindles displayed a dramatic increase in MT length compared to those observed in cells transfected with KLP61F dsRNA alone. In addition, the individual MT fibers of cells transfected with siRNA targeting both KLP61F and KLP67A had abnormal monopolar spindles. These fibers were not only much longer than those observed in KLP61F depleted cells, but they were also bent and curved as those observed in mutant KLP67A embryos. The effect of KLP67A on MT length was observed as early as prometaphase and in some cases prophase.

Example 7

Subcellular Localization of Human KIF18A

The localization of human KIF18A protein was determined in human 3T39 fibroblasts. A GFP-tagged KIF18A transgene was localized to the ends of microtubules during telophase of mitosis. Immunohistochemical staining using anti-KIF18A antibodies revealed a similar localization pattern. The KIF18A peptide used to raise antisera consists of amino acid residues 492-507 of SEQ ID NO:2 (FIG. 17).

This is consistent with the staining pattern of KLP67A in *Drosophila* cells. This also demonstrates a type of cell that can be used to assay test compounds for their ability to alter KIF18A localization.

Example 8

Overexpression of Human KIF18A

To create a GFP-tagged KIF18A construct, the KIF18A open reading frame was PCR amplified from cDNA clone DKFZp434g2226 (Resource Center/Primary Database; Berlin, Germany). The 5' ("Forward") primer contained a Xho I restriction site and the 3' ("Reverse") primer contained a BamH I restriction site. Following PCR amplification, the resulting KIF18A cDNA was digested with the two enzymes, and the product was cloned into pEGFP-C3 (cat. #6082-1 Clontech; Palo Alto, Calif.). This placed the GFP-tagged KIF18A construct under the control of a CMV promoter. One half microgram of the plasmid in 1.5 µl FuGENE 6 Transfection Reagent (Roche; Indianapolis, Ind.) was transformed into human 3T39 fibroblast cells. The cells were allowed to recover for two days, before the effect on cell division was monitored by live confocal imaging. These recordings, recorded over 2-4 minute intervals, revealed that, in living cells, the MTs of monopolar spindle asters appeared to depolymerizing back to the centrosome. These results suggest that overexpression of GFP-KIF18A caused an increased rate of microtubule depolymerization during mitosis, a result that is consistent with the observation that loss of function mutations in the *Drosophila* ortholog KLP67A caused a decreased rate of MT depolymerization (supra).

Immunofluorescence staining of fixed cells revealed generally disorganized spindles in control and KIF18A transfected cells.

The method described can be used in assays to screen for compounds that inhibit KIF18A expression or activity. For example, a test compound is incubated with a cell that overexpresses a KIF18A polypeptide. A decrease in the rate of microtubule depolymerization-in the presence of the test compound indicates that the compound inhibits KIF18A expression or activity.

Example 9

Synthesis of a Human KIF18A Antibody

An anti-KIF18A antibody was raised against a polypeptide fragment defined by residues 492-507 of SEQ ID NO:2 (FIG. 17). The polypeptide was synthesized by the Molecular Biology Core facility, University of Massachusetts (Worcester, Mass.), and antibodies were generated in mice.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method for identifying a compound that modulates activity of a KIF18A polypeptide, the method comprising:
   a) obtaining a test cell containing a KIF18A polypeptide that is at least 95% identical to SEQ ID NO:2 and that localizes to the distal ends of astral microtubules in dividing cells, and a control cell containing said KIF18A polypeptide;
   b) incubating the test cell with a test compound; and
   c) detecting an altered localization of the KIF18A polypeptide in the test cell as compared to the KIF18A polypeptide in the control cell, wherein the altered localization is localization to a region other than a growth cone of an interphase cell or the distal ends of astral microtubules of a dividing cell,
   wherein an altered localization indicates that the test compound modulates activity of the KIF18A polypeptide.

2. The method of claim 1, wherein the KIF18A polypeptide has comprises the sequence of SEQ ID NO:2.

3. The method of claim 1, wherein the test compound is an antisense nucleic acid molecule, a small inhibitory RNA (siRNA), a ribozyme, a triple helix molecule, an antibody, a polypeptide, a peptoid, a polypeptide mimetic, a small inorganic molecule, or a small non-nucleic acid organic molecule.

4. The method of claim 1, wherein the polypeptide is localized to a region of a dividing cell other than the distal ends of astral microtubules in the presence of the test compound.

5. The method of claim 1, wherein the polypeptide is localized using immunocytochemistry.

6. The method of claim 1, wherein the polypeptide is fused to a reporter molecule.

7. The method of claim 6, wherein the reporter molecule is green fluorescent protein (GFP), β-glucuronidase (GUS), luciferase, chloramphenicol transacetylase (CAT), horseradish peroxidase (HRP), or β-galactosidase.

8. The method of claim 2, wherein the KIF18A polypeptide consists of the sequence of SEQ ID NO:2.

9. The method of claim 1, further comprising assaying spindle assembly or function of the test cell as compared to the control cell.

10. The method of claim 1, further comprising assaying cell division in the test cell as compared to the control cell.

11. The method of claim 1, further comprising determining whether the test compound binds to the KIF18A polypeptide.

12. The method of claim 7, wherein the reporter molecule is green fluorescent protein (GFP).

13. The method of claim 7, wherein the reporter molecule is β-glucuronidase (GUS).

14. The method of claim 7, wherein the reporter molecule is luciferase.

15. The method of claim 7, wherein the reporter molecule is chloramphenicol transacetylase (CAT).

16. The method of claim 7, wherein the reporter molecule is horseradish peroxidase (HRP).

17. The method of claim 7, wherein the reporter molecule is β-galactosidase.

* * * * *